US006291214B1

(12) United States Patent
Richards et al.

(10) Patent No.: US 6,291,214 B1
(45) Date of Patent: Sep. 18, 2001

(54) SYSTEM FOR GENERATING RECOMBINANT VIRUSES

(75) Inventors: Cynthia Ann Richards, Durham; Michael Phillip Weiner, Cary, both of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/309,382

(22) Filed: May 10, 1999

Related U.S. Application Data
(60) Provisional application No. 60/084,936, filed on May 11, 1998, now abandoned.

(51) Int. Cl.[7] .............................. C12N 15/64; C12N 5/02; C12N 15/63; C12N 1/21; C12N 1/19
(52) U.S. Cl. ...................... 435/91.4; 435/320.1; 435/325; 435/252.33; 435/254.21; 536/23.1; 536/24.1
(58) Field of Search .................... 536/23.1, 24.1, 536/24.2, 24.5; 514/44; 425/252.1, 235.1, 320.1, 325, 252.3, 91.4, 252.33, 254.21; 424/93.1

(56) References Cited

U.S. PATENT DOCUMENTS

| 5,348,886 | 9/1994 | Lee et al. ........................ 435/320.1 |
| 5,478,731 | * 12/1995 | Short .................................... 435/91.4 |
| 5,846,528 | * 12/1998 | Podsakoff et al. .................. 424/93.2 |
| 5,851,766 | * 12/1998 | Ryals et al. ............................ 435/6 |
| 6,004,797 | * 12/1999 | Colosi ................................ 435/235.1 |

OTHER PUBLICATIONS

Berkner, K. L., "Development of Adenovirus Vectors for the Expression of Heterologous Genes", Bio Techniques, (1988) 6, 616–629.

Ketner, G. et al., "Efficient Manipulation of the human adenovirus genome as an infectious yeast artifical chromosome clone", Proc. Natl. Acad. Sci USA 91 (1994) 6186–6190.

Chartier, C. et al., "Efficient Generation of Recombinant Adenovirus Vectors by Homologous Recombination in *Escherichia coli*", J. Virol 70, (1996) 4805–4810.

Crouzet, J. et al., "Recombinational construction in Escherichia of infectiuos adenoviral genomes", Proc. Natl. Acad. Sci. USA 94 (1997) 1414–1419.

He, T.–C, et al., "A Simplified system for generating recombinant adenoviruses", Proc Natl. Acad. Sci USA 95 (1998) 2509–2514.

Luckow, V. A. et al., "Efficient Generation of Infectious Recombinant Baculoviruses by Site–Specific Transposon–Mediated Insertion of Foreign Genes into a Baculovirus Genome Propagated in *Escherichia coli*", J. Virol 67, (1993) 4566–4579.

* cited by examiner

Primary Examiner—Robert A. Schwartzman
Assistant Examiner—Katharine F Davis
(74) Attorney, Agent, or Firm—Elizabeth Selby

(57) ABSTRACT

The present invention provides a system for simple generation of recombinant animal viruses. The system includes a virus homing vector and can further comprise a transfer vector. These components are used in a system that reduces the number of cloning steps and provides for easier preparation of a number of recombinant viruses.

49 Claims, 10 Drawing Sheets

1. Integrated 5' Cloning site
                         *Sfi*I
                 *Nco*I           *Srf*I

| | |
|---|---|
| SEQIDNO.:17 | AGGAGGAGGCCACCATGGCCC \| GGGCAGG... |
| SEQIDNO.:18 | TCCTCCTCCGGTGGTACCGGG \| CCCGTCC... |
| SEQIDNO.:19 |                       fMetAlaA    rgAlaGl —> βGal |

2. Clone into *Srf*I site with *Sfi*I/*Bam*HI adapters
             (5' PCR primer)             (3' PCR primer)

SEQIDNO.:20    5'-NNGGCCACCATGGCCNNN$_{20}$      *Bam*HI
                         *Sfi* I                       N$_{20}$CCTAGG-5'

3. Immediate expression and subcloning
                     *Sfi*I                *Sfi*I

| | |
|---|---|
| SEQIDNO.:21 | AGGAGGAGGCCACCATGGCCCNNGGCCACCATGGCCNNN... |
| SEQIDNO.:22 | TCCTCCTCCGGTGGTACCGGCNNCCGGTCCTACCGGNNN... |
| SEQIDNO.:23 |                     fMetAlaProGlyHisHisGlyProN... |

Leu           Leu
                                        His           His
                                        Gln           Gln
                                        Arg           Arg

4. Digest with *Sfi*I and intramolecular ligation

| | |
|---|---|
| SEQIDNO.:24 | AGGAGGAGGCCACCATGGCCNN... |
| SEQIDNO.:25 | TCCTCCTCCGGTGGTACCGGNN... |
| |                   fMetAlaNNN... |

FIG. 4C.

| 3' base(s) | Reading Frame | # amino acids added to C-terminus |
|---|---|---|
| TAG | 0 | 0 (precise) |
| TAC | 1 | 123 (44 + 79 βGal fusion) |
| TA | 2 | 42 (C-terminal fusion*) |
| T | 3 | 52 (not used) |
| TAGTA | 0 | 0 (Sup⁻ host) |
| TAGTA | 2 | 43 (Sup⁺ host) |

*TCS/MCS/Kemp/His6/TAATAA

```
                    (P_CMV)        CMV IE              BglII              Tn7 R
Seq.IDNo:10 3432 TGTGGGCGGA CAATAAAGTC TTAAACTGAA CAAAATAGAT CTAAACTTTG ACAATAAAGT CTTAAACTAG
            3502 ACAGAATAGT TGTAAACTGA AATCAGTCCA GTTATGCTGT GAAAAAGCAT ACTGGACTTT TGTTATGGCT
            3572 AAAGCAAACT CTTCATTTTC TGAAGTGCAA ATTGCCCGTC GTATTAAAGA GGGGCGTGGC CAAGGGCATG
                                                                        SacII          BglII
            3642 GTAAAGACTA TATTCGCGGC GTTGTGACAA TTTACCGAAC AACTCCGCGG ATTTAAATAG ATCTTGGAGA
                                               P_PH
            3712 TAATTAAATT GATAACCATC TCGCAAATAA ATAAGTATTT TACTGTTTTC GTAACAGTTT
            3772 TGTAATAAAA AAACCTATAA ATATTCCGGA TTATTCATAC CGTCCCACCA TCGGGCGCGG
                  SalI                         P_lac                SalI        P_T7
            3832 ATCGTCGACT TGACAATTAA TCATCGGCTC GTATAAT T TGTGG AA GTCGACTAAT ACGACTCACT
                                                                 RBS   Kozak fMet
                        XbaI           SacI                      SfiI  NcoI    SrfI/SmaI BamHI
            3897 ATCGGGATCT AGAAATATCT GAGCTCGTCT CGAATTAGGA GGAGGCCACC ATGGCC GGGCAGGGGATCC
                                                                  Seq.IDNo:11 >MetAlaA rgAlaGlyAspPr
                                                                         Seq.IDNo:12 >GlyArgGlySer
                      EcoRI    SacII   NotI        KpnI
            3967 ATGTACCCGC GTGGCAACGA ATTCTCCGCG GCCGCTCGAG GTACCTTACG TCGTGCTTCT CTGGGCAGAT
                 >oCysThrArg ValAlaThrA snSerProAr gProLeuGlu ValProTyrV alValLeuLe uTrpAlaAsp
                 >MetTyrProA rgGlyAsnGl uPheSerAla AlaAlaArgG lyThrLeuAr gArgAlaSer LeuGlyArgS
                      TCS           MCS                                        Kemptide
                                EcoRV
            4037 CCAAACGTCG TGGAGCGCTC GATATCCACC ACCATCATCA CCACTAATAA TCTTGGCGCG CCAAGGGTTA
                 >ProAsnValV alGluArgSe rIleSerThr ThrIleIleT hrThrAsnAs nLeuGlyAla ProArgValA
                 >erLysArgAr gGlyAlaLeu AspIleHisH isHisHisHi sHis******         βgal (a)
                      P_T3                         His6
            4107 ATTGCGCGCT TATGACCATG ATTACGGATT CACTGGCCGT CGTTTTACAA CGTCGTGACT GGGAAAACCC
                 >snCysAlaLe uMetThrMet IleThrAspS erLeuAlaVa lValLeuGln ArgArgAspT rpGluAsnPr
                                                                    PvuII
            4177 TGGCGTTACC CAACTTAATC GCCTTGCAGC ACATCCCCCT TTCGCCAGCT GGCGTAATAG CGAAGAGGCC
                 >oGlyValThr GlnLeuAsnA rgLeuAlaA laHisProPro PheAlaSerT rpArgAsnSe rGluGluAla
            4247 CGCACCGATC GCCCTTCCCA ACAGTTGCGC AGCCTGAATG GCGAATGGAG ATCCAATTTT TAAGTGTATA
                 >ArgThrAspA rgProSerGl nGlnLeuArg SerLeuAsnG lyGluTrpAr gSerAsnPhe ***
```

FIG. 7.

SEQUENCE LISTING

<160> NUMBER OF SEQ ID NOS: 26

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
ggtcgagcgt cttcgaagcg c                                              21

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 2
ccgtcttcga accaatcagc aaacc                                          25

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 3
ggttaattaa catcatcaat aatatacctt attttgg                             37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 4
ccagatctgc ttcgaaggcc ctagacaaat attacgc                             37

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
tcgacttaat taagatatcg cccgggcgcg atcgctctag aggtac                   46

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
ctctagagcg atcgcgcccg ggcgatatct taattaag                            38

```
<210> SEQ ID NO 7
<211> LENGTH: 13
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: SfiI enzyme
      recognition site

<400> SEQUENCE: 7
ggccnnnnng gcc                                                              13

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: recognition
      site

<400> SEQUENCE: 8
ggccaccatg gcccgggc                                                         18

<210> SEQ ID NO 9
<211> LENGTH: 15
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: synthetic
      oligonucleotide

<400> SEQUENCE: 9
nnggccacca tggcc                                                            15

<210> SEQ ID NO 10
<211> LENGTH: 885
<212> TYPE: DNA
<213> ORGANISM: Artificial Sequence
<220> FEATURE:
<223> OTHER INFORMATION: Description of Artificial Sequence: DNA:
      vector + lacZ encoding region
<220> FEATURE:
<221> NAME/KEY: CDS
<222> LOCATION: (516)..(875)

<400> SEQUENCE: 10
tgtgggcgga caataaagtc ttaaactgaa caaaatagat ctaaactttg acaataaagt      60
cttaaactag acagaatagt tgtaaactga atcagtcca gttatgctgt gaaaagcat       120 actggacttt tgttatggct aaagcaaact cttcattttc tgaagtgcaa attgcccgtc    180
gtattaaaga ggggcgtggc caagggcatg gtaaagacta tattcgcggc gttgtgacaa    240
tttaccgaac aactccgcgg atttaaatag atcttggaga taattaaatt gataaccatc    300
tcgcaaataa ataagtattt tactgttttc gtaacagttt tgtaataaaa aaacctataa    360
atattccgga ttattcatac cgtcccacca tcgggcgcgg atcgtcgact tgacaattaa    420
tcatcggctc gtataatttg tggaagtcga ctaatacgac tcactatcgg gatctagaaa    480
tatctgagct cgtctcgaat taggaggagg ccacc atg gcc cgg gca ggg gat        533
                                    Met Ala Arg Ala Gly Asp
                                     1               5 cca tgt acc cgc gtg gca acg aat tct ccg cgg ccg ctc gag gta cct      581
Pro Cys Thr Arg Val Ala Thr Asn Ser Pro Arg Pro Leu Glu Val Pro
       10                  15                  20
```

```
tac gtc gtg ctt ctc tgg gca gat cca aac gtc gtg gag cgc tcg ata      629
Tyr Val Val Leu Leu Trp Ala Asp Pro Asn Val Val Glu Arg Ser Ile
        25                  30                  35 tcc acc acc atc atc acc act aat aat ctt ggc gcg cca agg gtt aat      677
Ser Thr Thr Ile Ile Thr Thr Asn Asn Leu Gly Ala Pro Arg Val Asn
    40                  45                  50 tgc gcg ctt atg acc atg att acg gat tca ctg gcc gtc gtt tta caa      725
Cys Ala Leu Met Thr Met Ile Thr Asp Ser Leu Ala Val Val Leu Gln
 55                  60                  65                  70 cgt cgt gac tgg gaa aac cct ggc gtt acc caa ctt aat cgc ctt gca      773
Arg Arg Asp Trp Glu Asn Pro Gly Val Thr Gln Leu Asn Arg Leu Ala
                75                  80                  85 gca cat ccc cct ttc gcc agc tgg cgt aat agc gaa gag gcc cgc acc      821
Ala His Pro Pro Phe Ala Ser Trp Arg Asn Ser Glu Glu Ala Arg Thr
            90                  95                 100 gat cgc cct tcc caa cag ttg cgc agc ctg aat ggc gaa tgg aga tcc      869
Asp Arg Pro Ser Gln Gln Leu Arg Ser Leu Asn Gly Glu Trp Arg Ser
        105                 110                 115 aat ttt taagtgtata                                                    885
Asn Phe
    120

<210> SEQ ID NO 11
<211> LENGTH: 120
<212> TYPE: PRT
<213> ORGANISM: Artificial Sequence
<220> FEATURE:
<223> OTHER INFORMATION: Bgal fusion peptide

<400> SEQUENCE: 11

Met Ala Arg Ala Gly Asp Pro Cys Thr Arg Val Ala Thr Asn Ser Pro
 1               5                  10                  15

Arg Pro Leu Glu Val Pro Tyr Val Val Leu Leu Trp Ala Asp Pro Asn
            20                  25                  30

Val Val Glu Arg Ser Ile Ser Thr Thr Ile Ile Thr Thr Asn Asn Leu
        35                  40                  45

Gly Ala Pro Arg Val Asn Cys Ala Leu Met Thr Met Ile Thr Asp Ser
    50                  55                  60

Leu Ala Val Val Leu Gln Arg Arg Asp Trp Glu Asn Pro Gly Val Thr
 65                  70                  75                  80

Gln Leu Asn Arg Leu Ala Ala His Pro Pro Phe Ala Ser Trp Arg Asn
                85                  90                  95

Ser Glu Glu Ala Arg Thr Asp Arg Pro Ser Gln Gln Leu Arg Ser Leu
            100                 105                 110

Asn Gly Glu Trp Arg Ser Asn Phe
        115                 120

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence:
      fusion peptide <400> SEQUENCE: 12

Gly Arg Gly Ser Met Tyr Pro Arg Gly Asn Glu Phe Ser Ala Ala Ala
 1               5                  10                  15

Arg Gly Thr Leu Arg Arg Ala Ser Leu Gly Arg Ser Lys Arg Arg Gly
            20                  25                  30
```

```
Ala Leu Asp Ile His His His His His His
        35                  40
```

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: thrombin
      cleavage site

<400> SEQUENCE: 13

```
Met Tyr Pro Arg Gly Asn
 1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:
      cAMP-dependent protein kinase sequence

<400> SEQUENCE: 14

```
Leu Arg Arg Ala Ser Leu Gly
 1               5
```

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 15
gctctagaag gcaaacggcc ctcacgtcca agtggacg                    38

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 16
tccgtaaagc ggccgcattt aaatcatcat caataatata ccttaatttt ggatt    55

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: universal
      cloning site

<400> SEQUENCE: 17
aggaggaggc caccatggcc cgggcagg                               28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: universal
      cloning site

```
<400> SEQUENCE: 18
cctgcccggg ccatggtggc ctcctcct                                              28

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Bgal
      peptide

<400> SEQUENCE: 19

Met Ala Arg Ala Gly
 1               5

<210> SEQ ID NO 20
<211> LENGTH: 37
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: primer

<400> SEQUENCE: 20
nnggccacca tggccnnnnn nnnnnnnnnn nnnnnnn                                    37

<210> SEQ ID NO 21
<211> LENGTH: 39
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: synthetic
      oligonucleotide

<400> SEQUENCE: 21
aggaggaggc caccatggcc cnnggccacc atggccnnn                                  39

<210> SEQ ID NO 22
<211> LENGTH: 39
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: synthetic
      oligonucleotide

<400> SEQUENCE: 22
nnnggccatc ctggccnncg gccatggtgg cctcctcct                                  39

<210> SEQ ID NO 23
<211> LENGTH: 8
<212> TYPE: PRT
<213> ORGANISM: Artificial Sequence
<220> FEATURE:
<223> OTHER INFORMATION: Xaa at various positions may be Pro, Leu,
      His, Gln or Arg
<220> FEATURE:
<223> OTHER INFORMATION: Description of Artificial Sequence: peptide
      fragment

<400> SEQUENCE: 23

Met Ala Xaa Gly His His Gly Xaa
 1               5
```

```
<210> SEQ ID NO 24
<211> LENGTH: 22
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: synthetic
      oligonucleotide

<400> SEQUENCE: 24
aggaggaggc caccatggcc nn                                              22

<210> SEQ ID NO 25
<211> LENGTH: 22
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: synthetic
      oligonucleotide

<400> SEQUENCE: 25
nnggccatgg tggcctcctc ct                                              22

<210> SEQ ID NO 26
<211> LENGTH: 26
<212> TYPE: DNA
<213> ORGANISM: Artificial Sequence
<220> FEATURE:
<223> OTHER INFORMATION: n bases may be A, T, C, G, unknown or other
<220> FEATURE:
<223> OTHER INFORMATION: Description of Artificial Sequence: primer

<400> SEQUENCE: 26
ggatccnnnn nnnnnnnnnn nnnnnn                                          26
```

SYSTEM FOR GENERATING RECOMBINANT VIRUSES

This application claims priority to U.S. Provisional application No. 60/084,936 which was filed May 11, 1998 now abandoned.

BACKGROUND OF THE INVENTION

1. Field of the Invention

The present invention provides versatile vectors for efficient production of animal viral vectors carrying a nucleic acid of interest. Thus the vectors can be used to produce viral vectors for use in expression of nucleic acids, including production of RNA, antisense nucleic acids and polypeptides of interest.

2. Background

Adenoviruses (Ad) are 36 kb, linear, double-stranded DNA viruses that have been widely used for gene therapy, functional genetics, vaccines, and protein production (1–5). Most adenoviral vectors are based on the Ad type 5 (Ad5) viral backbone in which an expression cassette replaces the E1 and/or E3 region. Such E1−, E3− viruses are attractive vectors because they: i) can accept about 8 kb of exogenous DNA, ii) can be produced at very high titer in E1 complementing cells, and iii) are replication defective. Other attractive features of Ad vectors include infection of a wide range of both dividing and quiescent cell types at high efficiency, expression of genes at very high levels, and association with mild, self-limiting pathologies in humans (1–6). The increasing numbers of genes discovered by the human genome project, and the expanding field of gene therapy are driving a need for more efficient systems to generate recombinant Ad vectors to facilitate rapid, high throughput functional and therapeutic analysis.

Because of their complex genome, manipulation of Ad vectors to produce recombinant viruses has been difficult. Traditional methods of making recombinant adenoviruses use homologous recombination between two transfected DNAs in adenoviral-producing cell lines (6). The homologous recombination method is inefficient, time-consuming, and subject to contamination with replication-competent virus. Some newer methods of generating recombinant adenoviral vectors in yeast and E. coli have been reported (7–10). These methods shift the homologous recombination step from eukaryotic packaging cells into either yeast or E. coli. These newer methods allow the true cloning of the recombinant viral genome and thereby remove the need for clonal selection via repeated rounds of plaque purification. Although homologous recombination is quite efficient in yeast, it is desirable (because of the faster doubling time and ease of manipulation) to be able to do these steps in E. coli. However, homologous recombination in E. coli is not very efficient. Furthermore, homologous recombination with adenoviral sequences necessitates cloning each gene of interest into a vector that can only be used for adenoviral expression.

A method that has been used to construct recombinant baculoviruses in E. coli by Tn7-mediated site-specific transposition (11) has proven to be very efficient at generating recombinant baculoviruses. However, this system has several limitations.

The present invention overcomes many limitations on previous systems. Specifically, the present invention provides a Tn7-based transposition system for generating recombinant viruses, such as adenovirus, in E. coli. A low copy E. coli homing plasmid, containing a full length viral genome with lacZattTn7 inserted in a manner that does not interfere with later production of recombinant virus, has been constructed. The inventive system moves all sequences necessary for replication and selection in E. coli outside of the viral genome, allowing application to small animal viruses (Ad, AAV and retroviruses); there is no need for a selectable marker within the transposon allowing additional space for exogenous nucleic acid of interest; it allows construction of a variety of homing vectors for different viruses comprising different promoters such that one transfer vector can be used to express an exogenous DNA from numerous promoters in numerous viruses. Thus the system is very easy, rapid, and efficient, accommodates sizable DNA inserts, and generates truly clonal viruses. The homing vector system is easily adapted to allow subcloning into a single universal transfer vector that can be used to transpose genes into any of several different expression systems, thus facilitating cost-effective subcloning into a variety of vectors, including adenoviral, retroviral, adeno-associated viral, baculoviral and E. coli vectors.

SUMMARY OF THE INVENTION

The present invention provides an isolated nucleic acid, termed a homing vector, for generating a recombinant animal virus comprising a) an animal virus polynucleotide wherein the viral polynucleotide comprises viral elements sufficient for recombinant viral production in a host cell upon contact with replication proteins of the virus;

b) a transposon target site within the virus polynucleotide wherein location of the transposon target site within the virus polynucleotide does not prevent recombinant viral production in a host cell upon contact with viral replication proteins; and an origin of replication.

The present invention further provides transfer vector for transposition of an exogenous nucleic acid, comprising (a) a transposon having a cloning site between a left end of the transposon and a right end of the transposon;

(b) a bacterial origin of replication positioned outside of a region encompassed by the left end and the right end of the transposon; and a selectable marker.

The present invention further utilizes these two components in a system for generating recombinant animal viruses. Thus, the invention provides a kit as well as a method of producing a recombinant animal virus comprising (a) contacting (1) a nucleic acid for generating a recombinant animal virus wherein the nucleic acid comprises (i) an animal virus polynucleotide wherein the viral polynucleotide comprises viral elements sufficient for recombinant viral production in a host cell upon contact with replication proteins of the virus;

(ii) a transposon target site within the viral polynucleotide wherein location of the transposon target site within the viral polynucleotide does not prevent recombinant virus production in a host cell upon contact with viral replication proteins; and (iii) an origin of replication, in a cell under conditions suitable for transposition, with (2) a transfer vector, wherein the transfer vector comprises (i) a transposon that recognizes the transposon target site, (ii) an exogenous polynucleotide inserted between a left end of the transposon and a right end of the transposon, (iii) a bacterial origin of replication positioned outside of a region encompassed by the left end and the right end of the transposon, and (iv) a selectable marker, to produce a transposition product; and (b) transferring the transposition product into a cell comprising a viral replication protein, thereby producing the recombinant animal virus.

BRIEF DESCRIPTION OF THE DRAWINGS

FIGS. 4A–4C. Plasmids and Multiple Cloning sites. A. pFastbac1. showing features (Luckow et al.), B. pSK213. A series of synthetic oligonucleotides were cloned into pFast-Bac1 3' of the baculovirus polyhedrin promoter ($P_{bac}$), between the BamHI and HindIII sites. These oligonucleotides incorporated the following relevant regions downstream of the $P_{bac}$ (from 5' to 3'); T7 promoter ($P_{T7}$), the EcoRI isocaudamer Esp3I, E. coli Ribosome Binding Site (E.c.$_{RBS}$), SfiI, Kozak site, ATG start site, NcoI, SrfI, BamHI, Thrombin Cleavage Site (TCS), Multiple Cloning Site (MCS), Kemptide, His6, HindIII. PCR was used to generate a fragment of the lacZα gene from plasmid pBK-CMV (Stratagene). The PCR primers used to generate the lacZα gene were designed to incorporate a 3' T3 promoter ($P_{T3}$) and 3' T7 transcription termination sequence (T7tt). The generated fragment include the region between the $P_{T7}$ and 3' of the SV40 poly(A) site. This PCR fragment was cloned into the HindIII site of the modified pFastBac1. Site-directed mutagenesis (SDM) was used to delete a 3' duplicated poly (A) site in the vector. The sequence between the EcoRV and 5' side of the $P_{bac}$ (encoding the Gt$^r$ gene of pFastBac1) was replaced by a PCR-generated fragment encoding the Kn$^r$ gene of pBK-CMV. The CMV immediate-early enhancer/promoter and a chimeric intron ($P_{CMV,I/E}$) derived from the 5' donor site from the first intron of the human B globin gene and the branch and 3'-acceptor site from the intron of an immunoglobulin gene heavy chain variable region were amplified from pCI-Neo and cloned upstream of the Tn7R site as indicated (C). Precise fusion to SfiI site after SrfI-PCR cloning was achieved using universal cloning site by cloning into SrfI site (integrated 5' cloning site) with SfiI/BamHI adapters and immediate expression and subcloning followed by digestion with SfiI and intramolecular ligation. C. Universal cloning site allowing precise fusion to SfiI site after SrfI-PCR cloning.

FIG. 7. Controlling element, DNA and protein sequence surrounding the start of recombinant protein translation. The start site for protein translation (ATG) is at nucleotide 3947. Controlling elements include the CMV Intron/enhancer region (CMV IE), Tn7 right attachment site (Tn7R), polyhedron promoter ($P_{PH}$), lac promoter ($P_{lac}$), bacteriophage T7 promoter ($P_{T7}$), bacteriophage T3 promoter ($P_{T3}$) and (complete sequence not shown) CMV promoter ($P_{CMV}$), E.coli ribosome binding site (RBS), Thrombin cleavage site (TCS), multiple cloning site (MCS), polyhistidine coding sequence (His6) and the first and third translated reading frames corresponding to Bgal and the affinity tag fusion frames, respectively.

DETAILED DESCRIPTION OF THE INVENTION

Figure 1:
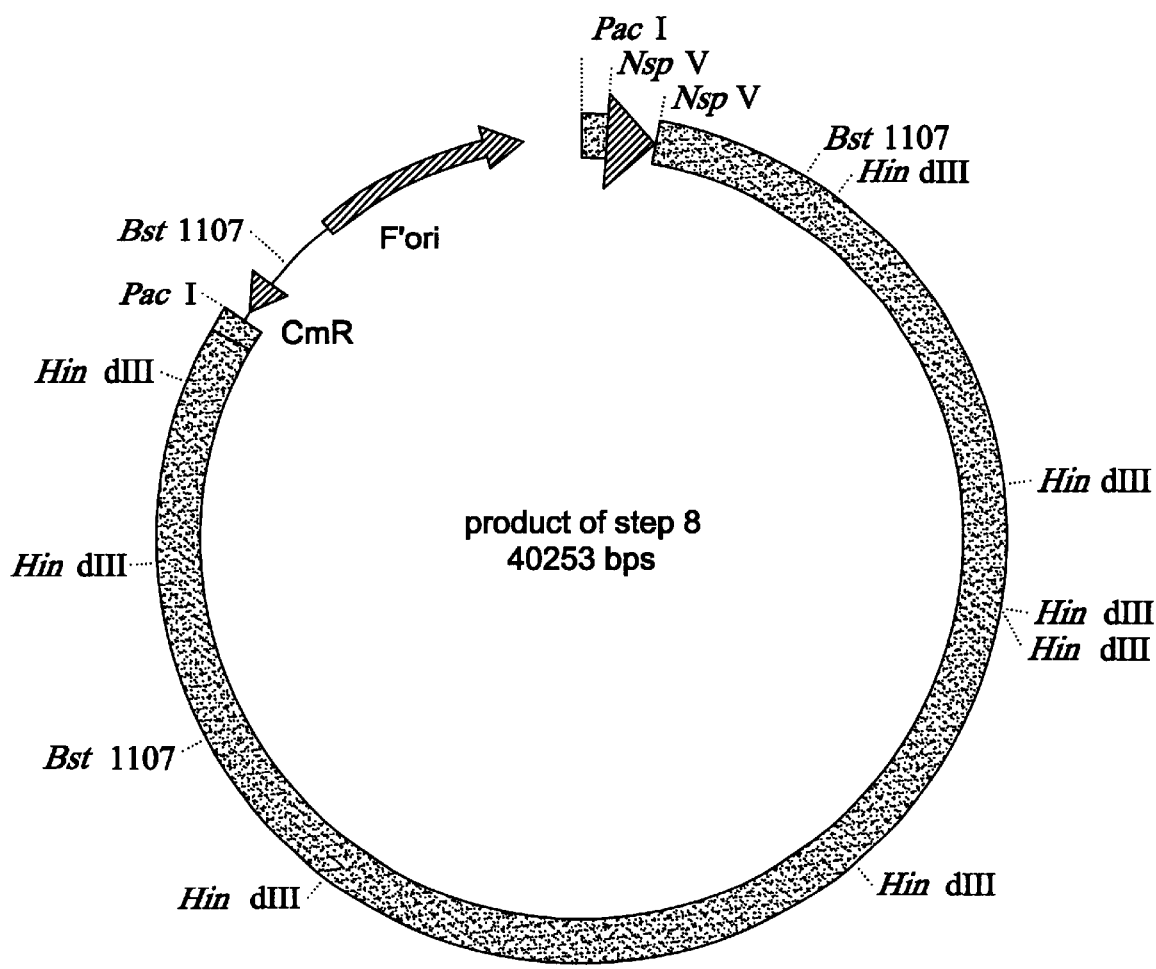
FIG. 1. Diagram of E1⁻, E3⁻ adenoviral homing vector. Solid boxes are sequences derived from Ad5. Large arrow head represents lacZattTn7 which is replacing E1 region. Small arrow head represents chloramphenicol resistance marker. Closed arrow represents F' origin of replication.

The present invention provides a system for simple generation of recombinant animal viruses. The system includes a virus homing vector comprising (1) an animal virus polynucleotide wherein the viral polynucleotide comprises viral elements sufficient for recombinant viral production in a host cell upon contact with replication proteins of the virus; (2) a transposon target site within the viral polynucleotide wherein location of the transposon target site within the viral polynucleotide does not prevent recombinant virus production in a host cell upon contact with viral replication proteins; and (3) an origin of replication The system further comprises a transfer vector for transposition of an exogenous nucleic acid, comprising (1) a transposon that recognizes the transposon target site, wherein the transposon has a cloning site between a left end of the transposon and a right end of the transposon; (2) a bacterial origin of replication positioned outside of a region encompassed by the left end and the right end of the transposon; and (3) a selectable marker. These components are used in a system that reduces the number of cloning steps and provides for easier preparation of a number of recombinant viruses.

As used in the claims, "a" and "an" can mean one or more, depending upon the context in which it is used.

The present invention provides an isolated nucleic acid for generating a recombinant animal virus comprising
a) an animal virus polynucleotide wherein the viral polynucleotide comprises viral elements sufficient for recombinant viral production in a host cell upon contact with replication proteins of the virus;
b) a transposon target site within the virus polynucleotide wherein location of the transposon target site within the virus polynucleotide does not prevent recombinant viral production in a host cell upon contact with viral replication proteins; and
an origin of replication.

The above nucleic acid, also termed "homing vector," can be prepared with any desired animal virus, such as, for example, adenovirus, retrovirus or adeno-associated virus. By animal virus is meant a virus that, when provided appropriate proteins (e.g., if replication deficient), can replicate in an animal or an animal cell. The present invention is particularly useful for adenovirus, retrovirus or adeno-associated virus-based vectors because the invention includes the placement of an origin of replication (for replication of the homing vector) outside the viral sequences rather than within the viral sequences, thus maximizing the size possible for an exogenous nucleic acid to be carried within the homing vector and, ultimately, a virus produced from the homing vector. In a preferred embodiment, a selection marker(s) (for maintaining the homing vector) is also placed outside the viral sequences in the homing vector. This choice of placement of an ori and any selectable markers allows space within the ultimately packaged virus for an exogenous insert, and it increases the size of exogenous nucleic acid insert one can place in the ultimately packaged virus. Thus, the present invention allows for better and additional uses of adenovirus, retrovirus and adeno-associated virus in particular that was not previously achievable. Furthermore, as can be seen from the examples, this invention can be readily applied to any desired animal virus to allow greater exogenous inserts to be transferred by viral vectors and to provide simpler production of virus once an exogenous gene of choice has been cloned into a transfer vector of this invention.

By "isolated" is meant separated "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

The homing vector is maintained in a host cell as a plasmid and, thus, can be maintained as a circular nucleic acid. However, as discussed below, the nucleic acid can be linearized prior to transfection of a packaging cell.

The term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein can refer to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The nucleic acid, or homing vector, can further comprise an indicator gene within the viral polynucleotide wherein the indicator gene has a transposon target site within the indicator gene, wherein transposition of an exogenous nucleic acid into the transposon target site disrupts expression of the indicator gene, and wherein location of the indicator gene within the viral polynucleotide does not prevent recombinant viral production in a host cell upon contact with viral replication proteins Any standard indicator gene can be utilized, such as, for example, lacZ gene. Typically, an indicator gene is preferred for ease in identifying transposition events. However, transposition is efficient enough (e.g., in first 9 experiments (see Example 1), 9–40% of total transformants are transposition products) that bacteria containing transposition products can be screened by restriction digests of plasmid DNA or by PCR (presence of PCR product when one primer anneals to the homing vector and the other primer anneals within the mini-Tn7) in the absence of the indicator gene. With AAV vectors it will be preferred that the homing vector not include an indicator gene since total capacity of AAV vectors is approximately 4,700 bp. It is also generally preferred that retrovirus homing vectors omit an indicator, since retroviruses are generally limited to about 1,000 bp.

The nucleic acid includes an origin of replication. The origin can be any selected origin of replication, such as a bacterial origin or a yeast origin of replication, selected based upon the type of cell in which one intends to maintain the plasmid. Such selection of an appropriate origin of replication is standard in the art. For example, the origin of replication can be derived from a bacterial origin selected from the group consisting of F, colE1, p 15A and f1. The origin of replication can be derived from a yeast origin selected from the group consisting of cen3, cen4, cen and two micron. In a preferred embodiment, the origin of replication is inserted in a region outside of the viral polynucleotide, as exemplified herein.

The homing vector can further comprise a selection marker. In a preferred embodiment, the selection marker is advantageously placed in the homing vector in a region outside the viral polynucleotide, to allow additional insert size. For any homing vector or transfer vector of this invention, in general any desired selection marker can be utilized. For example, suitable selection markers can include antibiotic resistance (e.g., chloramphenicol resistance, tetracycline resistance, ampicillin resistance, kanamycin resistance), auxotrophic markers and cell-surface markers.

The homing vector also can comprise a functional promoter, wherein upon transposition of an exogenous nucleic acid into the transposon target site, the promoter is positioned to promote expression of the exogenous nucleic acid. The promoter can be a prokaryotic promoter or a eukaryotic promoter. A prokaryotic promoter would be useful on the transposed homing vector DNA but not in the ultimate virus produced. The virus should not deliver to prokaryotes where the promoter will be active. The nucleic acid can comprise one or more promoters (e.g., a series of promoters) positioned to promote expression of the exogenous nucleic acid upon transposition of the exogenous nucleic acid into the transposon target site. Thus, the promoter can be present in any of several regions within the nucleic acid, as will be recognized by those of skill in the art. For example, the promoter, or series of promoters, can be positioned within the transposition cassette or they can be positioned upstream of the transposon site. The latter position is particularly useful when one or more ATGs present in the transposon have been rendered non-functional. Typically, when there is present a series of promoters, each promoter functions in a different capacity; for example, each may function in a different type of host cell, they may produce different levels of expression within the same host cell type, or they may have different mechanisms of expression (e.g., one or more can be an inducible promoter). Thus, a series of promoters can be selected from, for example, a eukaryotic promoter such as tet-inducible, tet-repressible, ecdysone, baculovirus basic, baculovirus polyhedrin, CMV, SV40 or RSV promoter, or a prokaryotic promoter, such as T7, lac, tac, trp, or alkaline phosphatase promoter. The promoters in a series can be a combination of prokaryotic and eukaryotic promoters, preferably in a concatameric array. Such an arrangement of promoters is beneficially enhanced by the removal of intervening ATGs between the promoter (either on the transfer vector or on the homing vector) and the exogenous nucleic acid to increase translational initiation at the desired ATG site. For example, ATGs are found in Tn7, and one or more of these ATGs can be rendered non-functional, such as by site-specific mutagenesis. Additionally, one can use GTG in *E.coli* for the reporter so as to allow for the use of the protein ATG.

It is noted that one or more promoters can be brought into the ultimate virus in a transfer vector, or one or more promoters can be brought in on a homing vector, exogenous to the transposition cassette, or a combination of both can be done.

The transposon and corresponding transposon attachment or recognition site can be any desired transposon. For example, the Tn7 transposon and transposon attachment site can be utilized. The transposon attachment site (target site) can be located within the homing vector in any region that does not prevent recombinant virus production upon placing the vector in appropriate packaging. For example, for adenovirus, the transposon target site can be located, e.g., in place of part or all of E1, E2, E3, and/or E4.

The virus can be any selected animal virus. For example, the virus can be adenovirus. Several adenoviruses can be utilized, such as Ad2, Ad4, Ad5, and Ad7, which are known in the art. In particular, Ad4 and Ad7 have been used as live viral vaccines in humans. Additionally, Ad 2 (Genbank accession J01917) and Ad5 (GenBank accession M73260) (exemplified herein) are greater than 90% similar in DNA sequence homology. (see, e.g., BioTechniques 6, 616–629 (1988); Vaccine 13, 1143–1151 (1995); Adenoviruses in Encyclopedia of Virology, ed. R. Webster and A. Granoff Academic Press).

The E1 region of adenovirus can be deleted from the adenoviral polynucleotide. The E3 region of adenovirus can be deleted from the adenoviral polynucleotide. The E1 region and the E3 region of adenovirus can be deleted from the adenoviral polynucleotide. The E2 or E4 region of adenovirus can be deleted from the adenoviral polynucleotide. E3 is not necessary for replication of Ads in cell culture, thus is it not necessary to provide E3 in trans. These deleted region(s) can be utilized as a site for insertion of a transposon attachment site, if desired. Additionally, if an indicator gene is utilized in the homing vector, one or more of these regions, e.g. E1, can be replaced with the indicator gene. For E4 deletions it has been reported that it is advantageous to add spacer DNA into the deleted E4 region to maintain adequate expression of fiber for high titre virus production (J Virol. 70, 6497–6501 (1996). To maximize the amount of exogenous DNA that can be transposed into E4, E3, E1 deleted Ads, it can be desirable to locate transposon target site in the E4 region.

The homing vector can further comprise a transposon inserted into the transposon target site, wherein the transposon comprises an exogenous polynucleotide. The an exogenous polynucleotide can encode a polypeptide (e.g., reporter genes); it can encode an antisense nucleic acid (see, e.g., Antisense DNA and RNA, D. A. Melton, Ed. Cold Spring Harbor Laboratory, Cold Spring Harbor, N.Y. (1988)); it can encode an aptamer; it can encode a DNA binding site (e.g., to titrate out transcription factors), for example. As is known in the art, aptamers are DNA/RNA molecules that can assume a (stable) 3-D shape that interferes with protein function. (Annu. Rev. Biochem. 64,763–797 (1995); J. Biol. Chem 23,13581–13584 (1995). The length of the exogenous nucleic acid can be selected bearing in mind the packaging capacity of the homing vector into which the exogenous nucleic acid will be transposed, such that the resulting recombinant virus can be packaged. In one embodiment, the exogenous nucleic acid lacks its own promoter; in such a embodiment, the transfer vector and/or the homing vector ultimately supplies a promoter. The transfer vector can additionally provide other components for functional expression of the exogenous nucleic acid, or they can be cloned in with the exogenous nucleic acid. Such components are known on the art and can include, for example, processing sites such as a polyadenylation signal, ribosome binding sites, RNA splice sites, and transcriptional termination sequences.

It can be advantageous to make adenovirus-based homing vectors with mutated (or use wt genes from other serotypes) fiber, penton, hexon genes to alter tropism of virus. For example it has been shown that mutating the fiber gene can direct Ads to infect cells via binding to heparan-containing cellular receptors. Nature Biotechnology 14,1570–1573 (1996) The animal virus can also be a retrovirus. Replication-defective retroviral shuttle vectors and complementing retroviral producing cell lines are well-known in the art, for example, the retroviral vectors pLNCX, pLNX, and N2 and the retroviral packaging cell line PA317. Retroviral homing vectors need to contain appropriate retroviral regulatory sequences for viral encapsidation, proviral insertion into the target genome, and message splicing, termination, and polyadenylation. For efficient packaging, retroviral genomes should in general be less than about 11,000 bp. The gag, pol, and env genes do not need to be present on the retroviral homing vector because they can be provided in trans by specially designed retroviral producing cell lines. Retroviral homing vectors can be made from existing retroviral shuttle vectors by standard molecular biology techniques well-known to those skilled in the art and as exemplified in the examples herein. One can generate a retroviral homing vector designed to have the regulatory sequences expressing the transposed DNA within the transposition cassette. Alternatively, one can generate a retroviral homing vector designed to have the regulatory sequences controlling the expression of the transposed DNA outside the transposition cassette Because retroviruses have an RNA genome it maybe necessary to remove the introns from the mini-Tn7s of transfer vectors which are used with retroviral homing vectors in order to avoid inadvertent splicing of the recombinant retroviral genome prior to packaging. (se, e.g., BioTechniques 7, 980–990 (1989); European patent application 0 415 731 A2).

Another viral expression system that can be adapted to for use with homing and transfer vectors is adeno-associated virus (AAV). The cis-acting DNA sequences necessary for generating AAV are the short ITRs. All gene products can be provided in trans.

The present invention also provides a cell comprising the homing vector. The cell can be any cell capable of replicating the homing vector. For example, the cell can be a bacteria, yeast, *E. coli, S. cerevisiae* cell. The cell can also be a cell capable of production of the virus; i.e., a cell providing any necessary replication proteins, such as replication proteins not encoded on the homing vector. Appropriate cell are known in the art. For example, for replication of El deleted Ads: HEK 293 (more commonly referred to as just 293) (J. Gen. Virol. 36, 59–72 (1977); for replication of E1 and E4 deleted Ads: 293-ORF6 cells (J Virol. 70, 6497–6501(1996) [Genvec]); for replication of E1, E2b deleted Ads: B-6 (J Virology 72, 926–933 (1998)) can be used.

Using coinfection with a packaging impaired helper virus SV5 it has been possible to delete all viral genes from an Ad vector. The only essential Ad sequences needed on the Ad vector are the viral origin of replication and packaging signal. The required sequences are located on the 358bp left end of Ad. These vectors require large inserts to keep the final genome size near that of a wild-type Ad. (Proc. Natl. Acad Sci. 93, 5731–5736, (1996); Nature Medicine 2, 714–716 (1996)).

The present invention further provides a transfer vector for transposition of an exogenous nucleic acid comprising
    a transposon having a cloning site between a left end of the transposon and a right end of the transposon;
a bacterial origin of replication positioned outside of a region encompassed by the left end and the right end of the transposon; and
    a selectable marker.

The transposon can be, for example, Tn7, Cre-lox, lambda integrase, or other viral integrase genes. In one embodiment, the selectable marker is inserted outside of the region encompassed by the left end and the right end of the transposon. In another embodiment, a functional ATG codon within the transposon has been rendered nonfunctional. In such an embodiment, an exogenous nucleic acid inserted into the cloning site can lack a promoter; thus a different promoter can be placed, either in the transfer vector and/or in the ultimate homing vector, to promote expression of the exogenous nucleic acid, reading through the transposon.

In another embodiment, the transfer vector further comprises a promoter outside the region encompassed by the left end and the right end of the transposon, positioned to promote expression of an exogenous nucleic acid inserted in the cloning site. As described above for the homing vector, the promoter can be one or more promoters, derived from one or more organisms. For example, the promoter can be a cytomegalovirus promoter, inserted wither inside or outside of the left end or the right end of transposon, and positioned to read in the direction of the cloning site into which an exogenous nucleic acid can be cloned.

Exogenous polynucleotides can be selected as described above. The selectable marker can be any desired selectable marker, as described above. The selectable marker can be placed outside of the left end and the right end of the transposon, so that ultimately, fewer nucleic acids are transposed into the homing vector. However, the selectable marker can be placed within the left end and the right end of the transposon; when it is so placed, it is preferred that the direction of promotion of the selectable marker be the same direction of the promoter for the exogenous gene, and further, that the selectable marker be placed 3', or downstream, of the exogenous nucleic acid.

The present invention additionally provides a cell comprising a transfer vector of this invention. Such cells can be any selected cell that can replicate the vector, such as a bacterial cell (e.g., *E. coli*) or a yeast cell (e.g., *S. cerevisiae*).

The present invention additionally provides a kit comprising a nucleic acid for generating a recombinant animal virus comprising
    (1) an animal virus polynucleotide wherein the viral polynucleotide comprises viral elements sufficient for recombinant viral production in a host cell upon contact with replication proteins of the virus; a transposon target site within the viral polynucleotide wherein location of the transposon target site within the viral polynucleotide does not prevent recombinant virus production in a host cell upon contact with viral replication proteins; and an origin of replication; and
    (2) a vector for transposition of an exogenous nucleic acid, comprising a transposon that recognizes the transposon target site, wherein the transposon has a cloning site between a left end of the transposon and a right end of the transposon; a bacterial origin of replication positioned outside of a region encompassed by the left end and the right end of the transposon; and a selectable marker. A kit can include a host containing a homing vector and transposase helper functions, and further wherein the host cell is competent for transformation.

The present invention further provides a method of producing a recombinant animal virus comprising
    (a) contacting a homing vector (as described herein), in a cell under conditions suitable for transposition, with a transfer vector, wherein the transfer vector comprises
        (i) a transposon that recognizes the transposon target site,
        (ii) an exogenous polynucleotide inserted between a left end of the transposon and a right end of the transposon,
        (iii) a bacterial origin of replication positioned outside of a region encompassed by the left end and the right end of the transposon, and
        (iv) a selectable marker,
    to produce a transposition product; and
    (b) transferring the transposition product into a cell comprising a viral replication protein,
    thereby producing the recombinant animal virus.
As described herein, the homing vector comprises a nucleic acid for generating a recombinant animal virus comprising a) an animal virus polynucleotide wherein the viral polynucleotide comprises viral elements sufficient for recombinant viral production in a host cell upon contact with replication proteins of the virus;
b) a transposon target site within the viral polynucleotide wherein location of the transposon target site within the viral polynucleotide does not prevent recombinant virus production in a host cell upon contact with viral replication proteins; and
c) an origin of replication.

The contacting step can be achieved by standard transfer of the homing vector and the transfer vector into a cell. Such standard means can include, for example, using chemically competent cells, electroporation, and the like. The cell is typically a prokaryotic cell, or it can be a yeast cell. The cell preferably also contains or has transferred into it, genes encoding any necessary proteins, such as a transposase gene. The cells are maintained under conditions that will allow transposition to occur, including conditions that allow production of the transposase. Once a transposition product has formed, it can be harvested from the transposition cell and then transferred into a cell capable of producing the virus of the homing vector, as described above. For example, for adenovirus having a deletion of E1, 293 cells can be utilized. The transfer can be achieved by any of several standard methods such as calcium phosphate treated cells, electroporation or liposome-mediated transfer. The cells can be maintained under conditions that allow production of the virus, and recombinant virus can be harvested.

As described above, in this method, the nucleic acid can further comprise a promoter inserted in a region within the viral polynucleotide and positioned to promote expression of the exogenous polynucleotide. In particular, the nucleic acid can further comprise a promoter inserted in a region outside of the transposition target site and positioned to promote expression of the exogenous polynucleotide. Additionally, the exogenous polynucleotide can lack a promoter. In this embodiment, it is preferred, but not required, that a functional ATG codon within the transposon have been rendered non-functional.

The transfer vector can further comprise a promoter outside the region encompassed by the left end and the right end of the transposon, positioned to promote expression of an exogenous polynucleotide inserted in the cloning site. In this embodiment, the exogenous polynucleotide can lack a promoter, and additionally or alternatively, a functional ATG codon within the transposon can have been rendered non-functional. In this embodiment, the homing vector will typically provide the promoter. As described above, the promoter can comprise two or more promoters derived from two or more organisms.

In one embodiment, the transfer vector further comprises a promoter within the region encompassed by the left end and the right end of the transposon, positioned to promote expression of an exogenous polynucleotide inserted in the cloning site. In one specific embodiment the promoter is a cytomegalovirus promoter.

This method of producing a recombinant animal virus can be utilized for many purposes, as the skilled artisan will recognize. For example, expression of a gene of interest can be monitored in several cell types, with only one cloning of the gene of interest necessary. The recombinant viruses can ultimately be administered to a cell, a tissue, an organ or a subject of interest. For example, the subject can be a mammal, such as a human, a veterinary animal, such as a cat, dog, horse, pig, goat, sheep, or cow, or a laboratory animal such as a mouse, rat, rabbit, or guinea pig. The promoter, whether provided on the homing vector or otherwise, can be selected accordingly for expression in the selected cell type. Administration to the cell, tissue, organ or subject of the virus can be by standard means for that subject. The administration can provide a protein to a subject in need of the protein, for example, or an antisense nucleic acid to inhibit expression of a gene.

The present invention will be illustrated in detail in the following examples, which examples are not intended to limit the present invention.

EXAMPLES

Bacterial strains, plasmids, cell lines and viral DNAs. DH10B and DH10Bac competent cells and pFASTBAC1 were obtained from Life Technologies [(LTI), Gaithersburg, Md.]. The plasmid pMON7124 (13) was isolated from DH10Bac cells. BJ5183 (14) were provided by D. Hanahan. pGL3-basic was purchased from Promega Madison, Wis.). The tetracycline regulateable promoter (TetOp) and tetracycline-regulated transactivator (tTA) were obtained from H. Bujard (15). P. Fasani-Ghersa (Serono, Geneva, Switzerland) constructed and made available to us AdtTA. Other reagents include: pFOS1 (16), IN340 viral DNA (17), HEK 293 cells (18), and IMR-90 cells (19).

General Methods.

Competent cells were prepared by the $CaCl_2$ method and stored frozen (20). Plasmid minipreps were prepared using Wizard minipreps (Promega); plasmids >20 kb were eluted from the minicolumns with 80° C. water. For large scale isolation of admids, 500–1000 ml cultures were grown in LB and the admid isolated using plasmid maxi kits using the procedure recommended for low-copy plasmids (Qiagen, Valencia, Calif.). LB agar was supplemented with 100 μg/ml ampicillin (Ap), 15 μg/ml tetracycline (Tc), 20 μg/ml chloramphenicol (Cm), 7 μg/ml gentamycin (Gm), 300 μg/ml Bluo-gal (LTI), and 40 μg/ml isopropylthio-β-galactoside (IPTG) as indicated. Polymerase chain reaction (PCR) was performed with Ampli-Taq (Perkin Elmer, Foster City, Calif.) using standard techniques (20).

Example 1

Construction of Adenoviral (Admid) Homing Vectors and Transfer Vectors.

A. One synthetic route to constructing an admid is described hereafter. However, those skilled in the art will realize, that many other routes can be used to obtain a functionally identical endpoint. It is possible to locate the lacZattTn7 site in a different location within the admid, e.g. replacing the E3 region. Furthermore, additional adenoviral sequences can be deleted depending on the cell line used to produce virus from the admid constructs, e.g. E4 could be deleted if the admid was amplified in 293-ORF6 cells [Brough et al. J. Virol. 70, 6497–6501 (1996)]. Standard molecular biology techniques widely known to those skilled in the art are used throughout the example. Many of these molecular biology techniques are described in books such as *Current Protocols in Molecular Biology*.

Step 1.

The left end of the adenoviral genome is obtained by Polymerase Chain Reaction (PCR) amplification. The template DNA is purified viral DNA of Ad5 strain IN340 [Hearing and Shenk, Cell 33, 695–703 (1983)] and the primers are priCR49 5'-GGTTAATTAACATCATCAATAATATACCTTATTTT GG (SEQ ID NO:3) and priCR50 5'-CCAGATCTGCTTCGAAGGCCCTAGACAAATATTA CGC (SEQ ID NO:4). The product of this amplification includes Ad5 bases 1–355 (all Ad5 coordinates based on GenBank accession M73260). The Ad5 sequences are flanked on the left side by PacI and on the right side by NspV and BglII restriction endonuclease recognition sites. The PCR product is cloned into the plasmid vector pGEM-T Easy (Promega Corporation). The plasmids from individual colonies are screened for the presence and orientation of the PCR product. Selected plasmids with inserts orientated such that the BglII site is closer to SalI rather than AatII are DNA sequenced to confirm that they contain complete and accurate copies of Ad5 coordinates 1–355 and the three introduced restriction endonuclease recognition sequences. A plasmid with the correct sequences is designated product of step 1 (pCR267).

Step 2.

The product of step 1 is further modified by inserting a 5.6 kb BglII restriction endonuclease fragment from IN340 (Ad5 coordinates 3328–8914) into the BglII site. Transformants are screened for a plasmid with the BglII fragment in the desired orientation, Ad5 base 355 closest to Ad5 base 3328. A plasmid, designated product of step 2 (pCR268), was identified that contains a PacI site 5' of Ad sequences 1–355, a NspV site, and Ad5 sequences 3328–8918. This plasmid resembles many standard E1 replacement adenovirus transfer vectors such as pQB1-AdBN (Quantum Biotechnologies Inc.) and pXCX2 [Spessot et al. Virology 168, 378–387 (1989)].

Step 3.

The product of step 2 is digested with the restriction endonucleases SalI and KpnI and the 8.6 kb fragment is isolated. An oligonucleotide adaptor, CRX/Y is created by denaturing and then slowly cooling the oligonucleotides CRX 5'-TCGACTTAATTAAGATATCGCCCGGGCGCGATCG CT CTAGAGGTAC (SEQ ID NO:5) and CRY 5'-CTCTAGAGCGATCGCGCCCGGGCGATATCTTAA TTAAG (SEQ ID NO:6). The CRX/Y adaptor is ligated to the 8.6 kb SalI, KpnI fragment of the product of step 2 and colonies are screened to identify plasmids that contain the adaptor. The desired recombinant plasmid is designated the product of step 3.

Step 4.

The product of step 3 is digested with the restriction endonuclease AatII. The AatII digested DNA is treated with T4 DNA polymerase and dNTPs to repair the ends. A SalI oligonucleotide linker, 5'-CGGTCGACCG (New England Biolabs) is ligated to the repaired, AatII-digested product of step 3. Transformants are screened to identify plasmids that contain the linker. The desired recombinant plasmid is designated the product of step 4.

Step 5.

The right end of Ad5 IN340 viral DNA is amplified using PCR. The primers for the amplification are priCH5 5'-GCTCTAGAAGGCAAACGGCCCTCACGTCCAAGT GGACG (SEQ ID NO.:15) and priCH6 5'-TCCGTAAAGCGGCCGCATTTAAATCATCATCAAT AATATACCTTAATTTTG GATT (SEQ ID NO.: 16). The PCR product is cloned into a vector such as pGEM-T Easy. The transformants are screened for plasmids that contain the PCR product. The inserts in selected plasmids are DNA sequenced to identify one containing a complete and accurate copy of the IN340 DNA. The approximately 1.7 kb SwaI, XbaI fragment is isolated from a sequence-verified pGEM-T Easy clone. The product of step 4 is digested with the restriction endonucleases EcoRV and XbaI and the 8.6 kb fragment is isolated. The 1.7 kb SwaI, XbaI fragment is ligated to the 8.6 kb EcoRV, XbaI fragment. Transformants are screened to identify plasmids that contain an accurate joining of the two fragments. The desired recombinant plasmid is designated the product of step 5.

Step 6.

The product of step 5 is digested with the restriction endonuclease SalI and the 7.3 kb fragment is isolated. The plasmid pFOS1 [Kim et al. Nuc. Acids Res. 20, 1083–1085 (1992)], is digested with the restriction endonuclease SalI and the 6.4 kb fragment is isolated. The two isolated SalI fragments are ligated. Chloramphenicol resistant transformants are screened for plasmids that have the Ad5 sequences of the product of step 5 linked to the F' origin derived from pFOS 1. The desired recombinant plasmid is designated the product of step 6.

Step 7

The lacZattTn7 can be obtained from PCR amplification using DNA isolated from DH10Bac (Life Technologies Inc.) and the primers priCRI 5'-GGTCGAGCGTCTTCGAAGCGC (SEQ ID NO:1) and priCR2 5'-CCGTCTTCGAACCAATCAGCAAACC (SEQ ID NO:2). The PCR product is cloned into a vector designed for cloning PCR products such as pGEM-T Easy. The transformants are screened for the presence of a 0.7 kb insert. The inserts in selected plasmids are DNA sequenced to confirm that they contain complete and accurate copies of lacZattTn7. The 0.7 kb NspV fragment is isolated from the pGEM-T Easy derivative and cloned into the NspV site of the product of step 6. The lacZattTn7 cassette is inserted between Ad5 base 355 and Ad5 base 3328. The product of step 7 containing the lacZattTn7 fragment converts E. coli DH10B from a βgal⁻ to a βgal⁺ phenotype on agar plates containing Bluo-gal and IPTG facilitating identification of the desired recombinant plasmid. Either orientation of the NspV site should be useful but a plasmid with lacZ in the same transcriptional orientation as E1 is designated the product of step 7.

Step 8.

The rest of the adenoviral genome can be added to the product of step 7 by homologous recombination in E. coli BJ5183 [Hanahan, D. J. Mol. Biol. 166, 557–580 (1983)]. The product of step 7 is digested with the restriction endonuclease HindIII and the 11.7 kb fragment is isolated. The 11.7 kb HindIII fragment of the product of step 7 is co-transformed with IN340 viral DNA into competent BJ5183. Chloramphenicol resistant colonies are screened for plasmids that contain a full-length admid that is designated the product of step 8. The adenovirus homing vector produced by this method is shown in FIG. 1.

B. An admid vector, pCR220, was constructed in a multistep procedure from IN340 viral DNA, bMON14272, and pFOS1. A PCR product comprising the lacZattTn7 (template: DH10Bac DNA; primers: priCRI 5'-GGTCGAGCGTCTTCGAAGCGC (SEQ ID NO:1) and priCR2 5'-CCGTCTTCGAACCAATCAGCAAACC) (SEQ ID NO:2) replaces about 3 kb of the E1A/E1B region of Ad5.

To generate a template for homologous recombination in E. coli, a plasmid, pCR207, was generated containing the left ITR of Ad5, the lacZattTn7 cassette, 2.4 kb of DNA from left end of Ad5 and 1.7 kb of DNA from the right end of Ad5. The plasmid pCR207 was linearized with the restriction enzyme Bstl107, separating the left end and right end homologies to Ad5 viral DNA, and was co-transformed with uncut IN340 viral DNA into competent E. coli BJ5183. Screening of the transformed cells identified pCR213, the product resulting from the homologous recombination between the input DNAs. The plasmid, pCR213 has a PacI site adjacent to the left end of the Ad genome and a SwaI site adjacent to the right end of the Ad genome. In a multistep procedure using standard cloning techniques, the β-lactamase gene and ColE1 origin of replication of pCR213 were replaced with the Cm resistance gene and the F' low-copy origin of replication from pFOS 1. These manipulations also resulted in the replacement of the SwaI site at the 3' end of the Ad genome with a second PacI site. The final construct, pCR220, is maintained as a low-copy plasmid in E. coli and produces a βgal⁺ phenotype on media containing Bluo-gal+IPTG. Restriction of pCR220 with PacI produces a linear DNA fragment that is essentially an E1⁻, E3⁻ recombinant adenoviral genome with lacZattTn7 replacing E1.

Although functionally deleted for E3, the E3 mutation in pCR220 is derived from dl309 in which the deleted Ad5 E3

DNA was replaced with heterologous DNA (21) resulting in little increase in the cloning capacity. To accommodate larger insert sizes it was desirable to remake the E3 mutation as a physical deletion of DNA. This was accomplished using standard DNA cloning techniques to replace the dl309-derived E3 mutation with an E3 mutation made by deleting the 1.9 kb XbaI fragment rom wild-type Ad5 creating pCR249. The Ad genome of pCR249 and pCR220 are 2.0 kb and 33.8 kb, respectively.

Plasmid transfer vectors containing mini-Tn7 elements (e.g., pCR259, FIG. 2) were constructed using standard cloning techniques. An admid transfer vector can be made by modifying pFASTBAC1 (Life Technologies Inc.) to contain an expression cassette that is active in target cells. For example the CMV immediate early promoter which is broadly active in most human and animal cells. One such admid transfer vector is pCR259. The vector was made by combining the CMV expression cassette from pCI (Promega Corporation) with the plasmid backbone and cis-acting Tn7L and Tn7R sequences from pFASTBAC1 (Life Technologies Inc.). Plasmid pCI was first digested with the restriction endonuclease BglII. The overhanging ends from the BglII-cleaved DNA were repaired using T4 DNA polymerase and dNTPs. Subsequently the linear pCI molecule was digested with the restriction endonuclease BamHI and the 1348bp DNA fragment was isolated. The plasmid pFASTBAC1 was first digested with the restriction endonuclease SacII. The overhanging ends from the SacII cleaved DNA were removed using T4 DNA polymerase and dNTPs. Ligation of the 1348bp BglII, BamHI fragment from pCI and the 3140bp BclII, SacII fragment of pFASTBAC1generated the plasmid pCR259.

It may also be desirable in some situations to use a promoter whose expression can be regulated. One example of such a promoter is the tetracycline-regulated promoter described by Gossen and Bujard [Proc. Natl. Acad. Sci. 89, 5547–5551 (1992)]. Admid transfer vectors containing the TetOp promoter can be made using standard molecular biology techniques to replace the CMV promoter of pCR259 with the TetOp promoter [440bp XhoI/SacII fragment of pUHG10-3, Ghersa et al. J. Biol. Chem. 269, 29129–29137, (1994)].

Transfer vectors containing the luciferase reporter gene, can readily be made by inserting the 1.7 kb HindIII, XbaI fragment of pGL3-basic into a cloning site (MCS) of the CMV or TetOp promoter. Vectors with a Tc-regulatable promoter can be made by replacing the CMV promoter with the 474 bp XhoI, XbaI fragment from pUHG10-3 (22) Construction of E. coli Strains DHiOB Admid220 and DH10B Admid249.

DH10B competent cells were transformed with extrachromosomal DNA isolated from DH1OBac and selected on Tc. Tc$^R$, Ap$^S$, kanamycin-sensitive colonies containing pMON7124 were isolated. Competent DH10B (pMON7124) cells were transformed with either pCR220 or pCR249. The transformants were plated on LB agar+Tc+Cm+Bluo-gal+IPTG and were designated DH10B (Admid220) and DH10B (Admid249), respectively.

Transposition of mini-Tn7 elements from transfer vectors into admids. Transposition was performed by transforming 80 μl competent DH10B Admid220 with 10 ng of uncut transfer vector. The competent cells were mixed with the transfer vector and incubated for 20 min on ice. Following a 45 second heat shock at 42° C. and a subsequent 2 min incubation on ice, 900 μl of S.O.C. media (LTI) was added and the cells were grown for 4 hours at 37° C. with aeration. The cultures were then plated on LB agar+Cm+Tc+Ap+Bluo-gal+IPTG and grown for 24 hrs at 37° C. The βgal⁻ transfonnants were verified as transposition products using PCR. A primer set, with one primer binding to the Ad sequences of the input admid and the other binding to an internal sequence of the mini-Tn7 of the transfer vector were used. Some of the transposed admid constructs were further verified via restriction enzyme digests after segregating the low-copy recombinant admid from the high-copy number pMON7124 helper plasmid and the transfer vector by CaCI$_2$ transformation.

Transfection of 293 Cells and Production and Purification of Adenovirus.

One day after plating about 2×10$^6$ cells per 60 mm dish, 293 cells were transfected using 2 μg plasmid DNA and 40 μg lipofectamine (LTI). The DNA/lipofectamine complex was incubated with the cells for 6 hrs in serum-free media before diluting the transfection mix with an equal volume of media containing 4% bovine calf serum. The cells were harvested after six days prior to any observed cytopathic effect. The cells were frozen and thawed three times, the cell debris pelleted and the virus-containing supernatant was titered and amplified.

Virus was titered by infecting confluent plates of 293 cells with virus dilutions for one hour. Eighteen hours later the cells were fixed with 90% methanol and the number of infected cells was determined by fluorescent microscopy [primary antibody: mouse Ab to adenovirus (Biodesign International, Kennebunk, Me.); secondary antibody: FITC-labeled goat anti-mouse antibody (ICN, Auroa, Ohio)]. Amplified virus was purified by standard techniques of banding in CsCl gradients (23).

Construction of Conventional Control Viruses.

The control viruses, AdCMV-null and Ad225, were constructed by the traditional method of homologous recombination in 293 cells (6). The recombinant viruses were identified by PCR analysis of the primary amplification of individual plaques, plaque purified again, and then amplified. The viruses were produced and purified the as described for the viruses produced using the admid system. Infection of Cell Lines and Luciferase Assays.

IMR-90 cells were plated at 5×10$^4$ cells/well in 6 well dishes. Two days later, after undergoing two population doublings, triplicate wells were infected with the indicated adenovirus mixtures at a total multiplicity of infection (MOI) of 100. Each infection contained 50 MOI of luciferase virus and 50 MOI of either AdCMV-null or AdtTA virus. Two days later the cells were harvested and assayed for luciferase activity using the luciferase assay system with cell culture lysis reagent as recommended by the supplier (Promega). Luciferase activity was quantitated using a ML3000 luminometer (Dynatech Labs, Chantilly, Va.). Where indicated the cell culture medium was supplemented with Tc starting one day prior to viral infection.

Example 2

Construction of Retroviral Homing Vectors and Transfer Vectors

To generate a retroviral homing vector designed to have the regulatory sequences expressing the transposed DNA within the transposition cassette, pLNCX can be digested with the restriction endonucleases BamHI and ClaI, and the DNA fragment comprising the LTRs isolated and subsequently ligated in the presence of an oligonucleotide adaptor that will reform the ClaI restriction endonuclease recognition site. A DNA fragment encoding a transposon target site, e.g. the lacZattTn7 NspV fragment from the product of step 8 of Example 1(A), can be subcloned into the ClaI restriction endonuclease site. Mini-Tn7s with desired promoters and exogenous sequences then can transpose into the lacZattTn7 in the presence of the trans-acting transposase gene products.

Retroviral homing vectors designed to have the regulatory sequences controlling the expression of the transposed DNA outside the transposition cassette can be made by adding the transposon target site in a suitable orientation downstream of a promoter. For example, pLNCX can be digested with ClaI and the lacZattTn7 cassette inserted such that the CMV promoter would control the expression of the transposed exogenous DNA The transfer vectors described in Example 1 above can be utilized in the retroviral homing vector system. Because retroviruses have an RNA genome it can be preferable to remove the introns from the mini-Tn7s of transfer vectors which are used with retroviral homing vectors in order to avoid inadvertent splicing of the recombinant retroviral genome prior to packaging. (see, in general, BioTechniques 7, 980–990 (1989); European patent application 0 415 731 A2). To produce retrovirus the retroviral homing vector is transfected into a retroviral producing cell line that provides the trans acting gag, pol, and env genes. The retroviral homing vector can be transfected either as a supercoiled DNA molecule or after digestion with a restriction endonuclease that cuts the DNA outside of the ecombinant retroviral genome. The choice of methods will be determined by several actors including whether or not the retroviral homing vector is to be maintained as an episome for high level transient and long-term expression, e.g. derived from vector such as LZRS-LacZ(A), or whether an integrated copy of the retroviral homing vector is desired, e.g. a stable PA317-derived cell line. In the first case uncut is preferred, in the latter case a linearized molecule is preferred.

Example 3
Construction of Adeno-Associated Viral Homing Vectors

An AAV homing vector can be made from a plasmid like pAAV/NEO [J. Virol. 63, 3822–3828 (1989)] by digesting the plasmid with the restriction endonuclease XbaI and replacing the SV-NEO cassette with a transposon target site. An AAV homing vector similar to pAAV/CMV/SIV rev-gp 160/rep-cap/neo [Human Gene Therapy 6, 1329–1341 (1995)], could be made by replacing the XbaI fragment containing the rep and cap genes of psub201 with either a DNA fragment comprising a promoter and a transposon target site or a transposon target site. The rep-cap cassette of pBS/rep-cap/neo could then be added into the AAV homing vector outside of the ITR, e.g. in the NgoMI restriction site of the pEMBL 8+plasmid backbone.

To produce AAV virus, the homing vector is transfected into a cell line that provides the trans acting rep and cap genes as well as a helper virus. The AAV homing vector can be transfected either as a supercoiled DNA molecule or after digestion with a restriction endonuclease that cuts the DNA outside of the recombinant AAV genome. The choice of methods will be determined by several factors including whether or not the viral production cells are intended to be transient or stable and the presence of a suitable restriction endonuclease recognition site. In transient transfections uncut DNA is preferred. To generate G418 resistant stable cell lines it is preferred to use linearized DNA if a suitable restriction endonuclease site is available.

Homing Vector Results
Construction of Plasmid Vectors.

Figure 2:
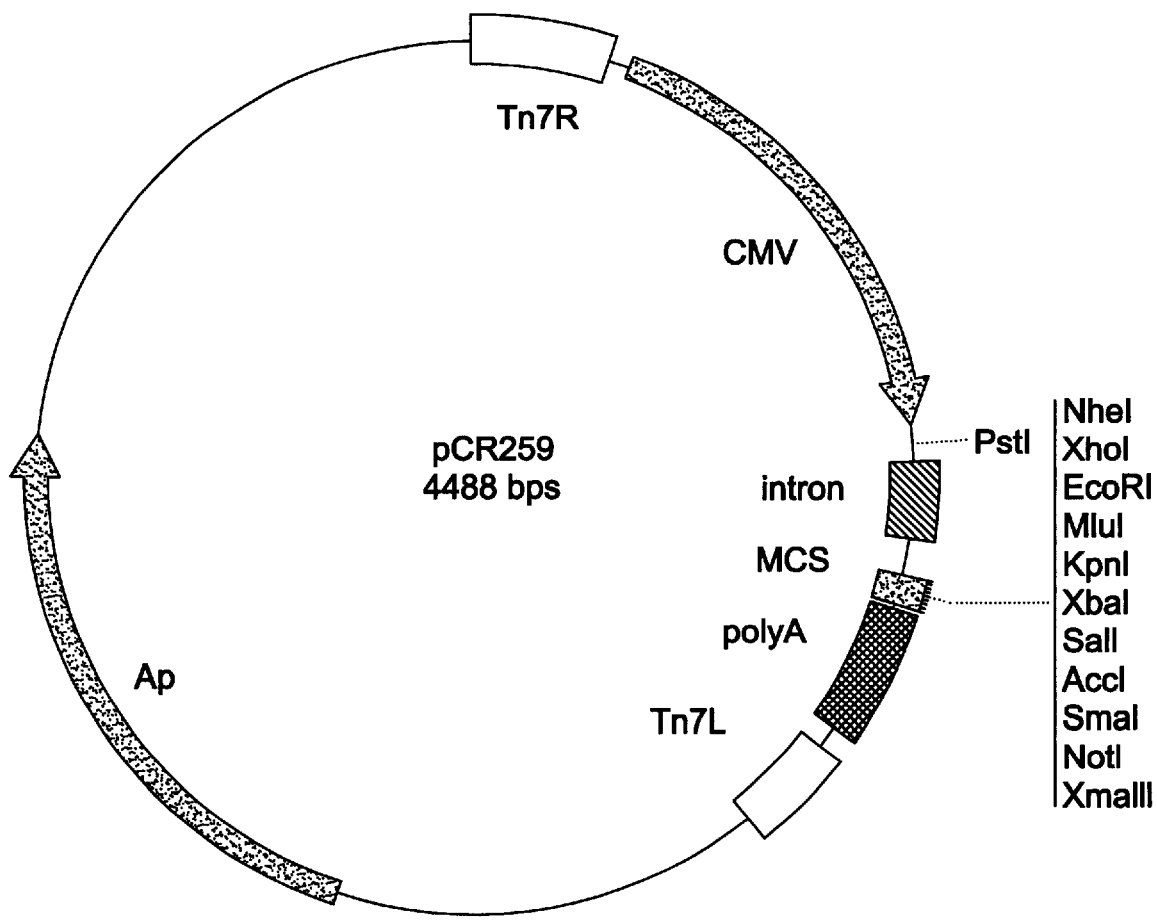
FIG. 2. Diagram of transfer vector PCR259. Tn7R and Tn7L, right and left ends of Tn7, respectively; hatched filled arrow, $AP^R$ gene; CMV, CMV promoter; MCS, multiple cloning site as labeled; poly A, polyadenylation signal of SV40.

The development of the present system required the construction of two plasmid components: i) a low-copy homing vector containing a viral genome with a lacZattTn7 site (FIG. 1), and ii) a transfer vector with a mini-Tn7 containing an expression cassette appropriate for expression in the selected viral vector (e.g., FIG. 2). For example, the admid pCR220 consists of an E1⁻, E3⁻ adenoviral genome that is replication-competent in complementing HEK 293 cells, but replication-deficient in cells lacking E1. The target site for Tn7 insertion, attTn7, is located in the lacZ gene. LacZ is disrupted by transposition into attTn7 and results in a βgal⁻ phenotype. The final construct is maintained as a low copy plasmid in E. coli to facilitate screening for the βgal⁻ phenotype. The βgal⁻ restriction sites that are located at each end of the adenoviral genome can be used to convert the recombinant adenoviral genome into a linear DNA. The admid pCR220 has the ability to accept about 4.1 kb of DNA in the transposed mini-Tn7 without exceeding the stable Ad packaging limit (24). Additional deletions of nonessential DNA allow about 6 kb to be transposed into pCR249.

The transfer vectors were designed to encode a mini-Tn7 transposition cassette that was as small as possible. The transfer vectors retain efficient transposition and provide transcriptional sequences for high level expression in mammalian cells. The cis-acting sequences required for Tn7 transposition, Tn7L and Tn7R, are only 0.2 kb and allow an additional 3.8 kb or 5.6 kb for transcriptional signals and coding sequences in pCR220 and pCR249, respectively. Several mini-Tn7 transfer vectors have been constructed (e.g., pCR259, FIG. 2). Convenient restriction sites are present in which to insert sequences under the control of the CMV or Tc-regulatable promoter. These sites may also be used to replace the CMV promoter with any other desired regulatory sequence.

Transposition and Confirmation of Transposition by PCR.

The host for transposition was an E. coli strain DH10B that contained the plasmid pMON7124 (encoding the trans-acting Tn7 transpose genes and Tc-resistance (13)), and an admid (containing the lacZattTn7 gene). Transposition occurs following introduction of a transfer vector containing a mini-Tn7 element into the host strain. Transposition into the lacZattTn7 site disrupts the lacZ gene and results in a βgal⁻ phenotype on media containing Bluo-gal and IPTG. This provides an easy way to identify the desired transposition products. Prior Tn7-based vectors have utilized a bacterial antibiotic marker within the mini-Tn7 to aid in the selection of transposed constructs. We have found, surprisingly, that the antibiotic marker within the Tn7 transposition cassette is unnecessary; similar transposition efficiencies were obtained whether or not an antibiotic marker within the mini-Tn7 cassette was used to select for the transposed constructs.

The results of nine independent transposition experiments are shown in Table 1. The percent of colonies exhibiting a βgal⁻ phenotype ranged from 9–40%. Transformation with the negative control plasmid pGL3-basic (a plasmid that does not contain any Tn7 elements), resulted in 100% βgal⁻ colonies. To confirm that the βgal⁻ colonies represented bonafide transposition events, white colonies were screened by PCR to confirm the insertion of the mini-Tn7 element into the attTn7 site. PCR confirmation was used for transposition experiments. The expected PCR fragment profile was observed for the transposition of the mini-Tn7 from pCR219 into pCR220. Restriction digests further confirmed that βgal⁻ colonies contained full-length admids with a mini-Tn7 insertion.

TABLE 1

Transposition efficiency in DH10B Admid220 cells

| Transfer vector | # βgal⁻ | # βgal⁺ | % βgal⁻ | # verified by PCR |
|---|---|---|---|---|
| pCR219 | 39 | 98 | 28.5 | 2/2 |
| pCR232 | 30 | 151 | 16.6 | 4/4 |
| ave 7 other constructs | 219 | 711 | 30.8 | 28/28 & 4/4[1] |
| pGL3-basic[2] | 0 | 900 | 0 | nt[3] |

[1]28/28 βgal⁻ colonies positive for transposition, 4/4 βgal⁺ colonies negative for transposition
[2]pGL3-basic contains no Tn7 elements
[3]nt, not tested Transfection Efficiency.

After clonal isolation of the βgal⁻ clones, admid DNA was isolated, and restricted with restriction enzyme PacI. Transfection of 293 packaging cells with admid DNA led to efficient production of infectious adenovirus (Table 2). Higher amounts of virus were produced if the cells were transfected with only the transposed recombinant admid DNA rather than a mixture of DNAs containing admid, transposase-helper, and transfer vectors. This likely reflects the increased molar amount of admid DNA available in 2 µg of pure admid DNA versus the lesser molar amount of the low-copy admid in the three-plasmid mixture with two high-copy number plasmids.

Results obtained with pCR213, a predecessor of admid pCR220 that contains a PacI site 5' and a SwaI site 3' of the Ad genome, demonstrated that virus was produced even if the admid DNA was not restricted prior to transfecting 293 cells. However, approximately 100-fold more virus was obtained from admid DNA that was restricted at either the right or both ends of the adenoviral genome than undigested admid DNA or admid DNA restricted only at the left end of their adenoviral genome (Table 2). These results demonstrate that it was not essential to linearize the recombinant admid before transfecting 293 cells. Therefore, there are no limitations with regard to any restriction sites that may be present in the gene of interest.

TABLE 2

Yield of Recombinant Adenovirus from 293 Transfection

| DNA | Treatment | location of restriction enzyme site[a] | PFU[b] |
|---|---|---|---|
| pCR220::Tn219 | PacI | 5', 3' | $5.7 \times 10^7$ |
| pCR220::Tn219/ pMON7124/pCR219 | PacI | 5', 3' | $7.7 \times 10^5$ |
| pCR220::Tn232 | PacI | 5', 3' | $3.4 \times 10^7$ |
| pCR220::Tn232/ pMON7124/pCR232 | PacI | 5', 3' | $8.5 \times 10^5$ |
| pCR249::Tn219 | PacI | 5', 3' | $3.4 \times 10^7$ |
| pCR249::Tn232 | PacI | 5', 3' | $9.0 \times 10^6$ |
| pCR213 | none | none | $7.6 \times 10^4$ |
| pCR213 | PacI | 5' | $6.8 \times 10^4$ |
| pCR213 | SwaI | 3' | $2.7 \times 10^7$ |
| pCR213 | PacI, SwaI | 5', 3' | $1.1 \times 10^7$ |

[a] relative to the ends of the Ad genome
[b] 60 mm dishes of 293 cells were transfected with 2 µg DNA using 40 µg lipofectamine, 5 days later monolayers were scraped from dish in 4 ml media, the suspension was frozen and thawed 3 times, and titered on 293 monolayers.

Titers and Expression from Admid Vectors.

We next compared titers and expression capabilities of vectors generated by conventional and admid methods. We constructed adenoviruses expressing luciferase by both the traditional method of homologous recombination in 293 cells and the admid method. The CMV-luciferase expression cassette is identical between Ad225 and Ad220::Tn219. Ad220::Tn219 differs from Ad225 in the addition of lacZ and Tn7 sequences flanking both sides of the CMV-luciferase expression cassette in Ad220::Tn219. When equivalent numbers of 293 cells were infected and the virus was purified, similar amounts of virus were obtained (Ad225, $9.2 \times 10^{10}$ pfu at $2.38 \times 10^{10}$ pfu/ml; Ad220::Tn219, $6.5 \times 10^{10}$ pfu at $1.14 \times 10^{10}$ pfu/ml; Ad249::Tn219, $6.6 \times 10^{10}$ pfu at $1.3 \times 10^{10}$ pfu/ml). Neither the titer nor the final yield of virus was altered by the lacZ or Tn7 sequences or the expanded E3 deletion.

Figure 3:
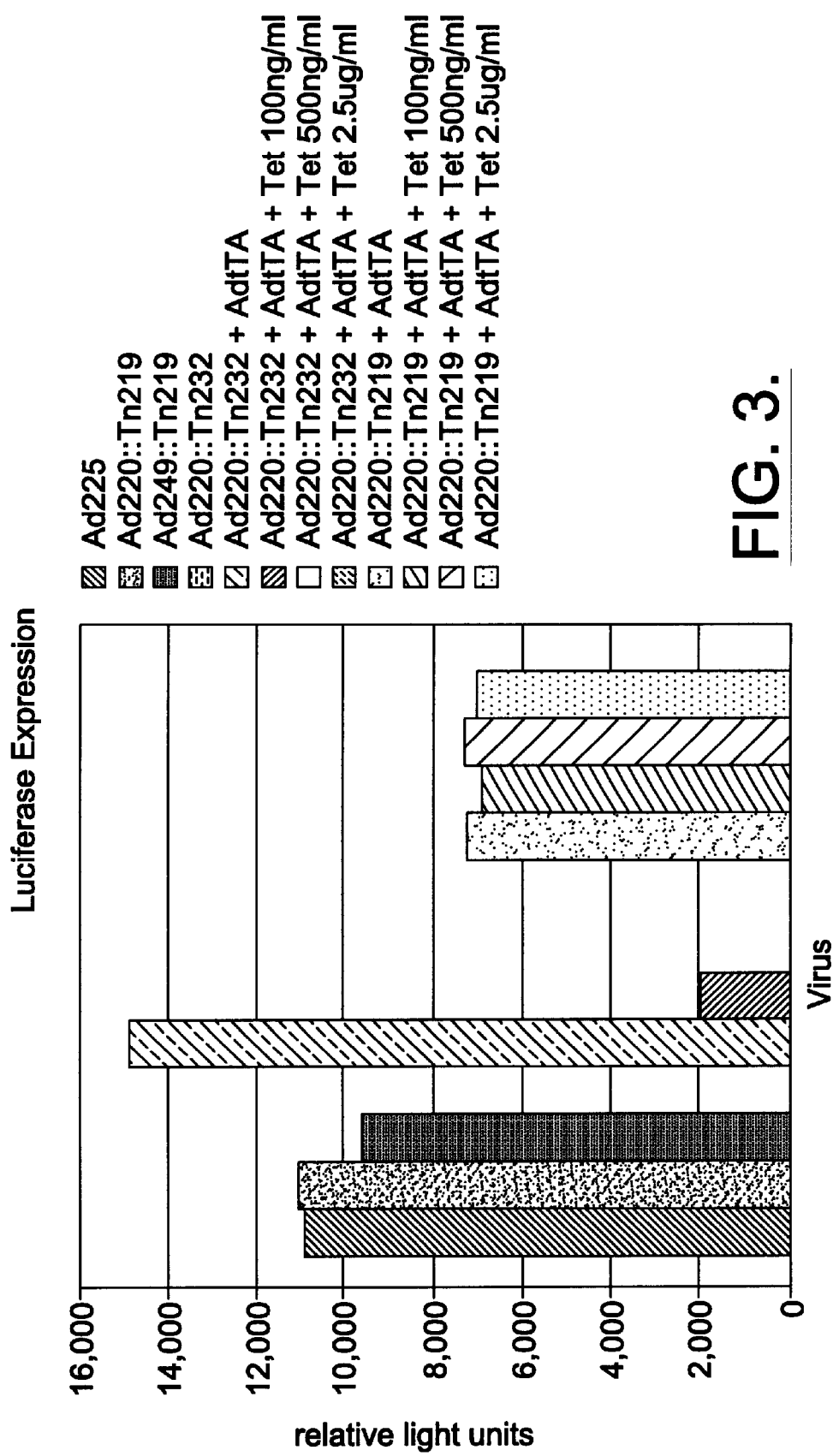
FIG. 3. Expression from luciferase recombinant Ads. Luciferase expression 48 hrs after infecting IMR-90 cells at an MOI of 100.

To test the expression levels obtained from each virus, IMR-90 cells were infected and the luciferase activity was quantitated (FIG. 3). A comparison of the luciferase activity from cells infected with either Ad225 or Ad220::Tn219 shows the same luciferase expression from viruses made by either method. This indicates that the flanking lacZ and Tn7 sequences do not affect the expression of the CMV promoter. Also as expected, the larger E3 deletion present in Ad249::Tn219 has no effect on CMV promoter activity.

Results obtained with cells infected with Ad220::Tn232+/− AdtTA demonstrate that the Tc-regulated gene expression system works very well. There is little to no expression detected in cells singly infected with either tetOp-luciferase virus (Ad220: :Tn232) or AdtTA transactivator virus. However, when these cells are co-infected with both viruses a very large amount of luciferase activity is observed. Furthermore adding Tc to the cell culture media allowed for the fine-tuning of the absolute level of luciferase expression. The ability to carefully control the level of expression of an introduced gene over such a broad range should facilitate functional analysis by allowing such studies to be carried out at physiological levels of gene expression.

Discussion

The present invention provides a method for generating recombinant viruses by transposon-mediated transposition in cells. The system is very fast, easy, and efficient. The transposition and screening for transposed homing vectors containing a mini-transposon expression cassette occurs in a single step that is both efficient and, when an indicator gene is utilized, easily scored, such as by a βgal⁻ phenotype on media containing Bluo-gal and IPTG. Every βgal⁻ colony we have screened has derived from a bonafide transposition event and each transposition experiment has yielded numerous transformants with between 9 and 40% of the transformants being βgal⁻, transposed admids (Table 1). This is in contrast to our experience with the E. coli BJ5183 homologous recombination system described by Chartier et al. (8). In particular, some previous homologous recombination attempts used homologous recombination in E. coli BJ5183. Although this method ultimately did work, it required several attempts and the screening of many colonies to identify the genuine homologous recombination product.

Several key differences exist between the design of the present viral homing and transfer vectors and the bacmid vectors (11). In the bacmid vector bMON14272, approximately 9 kb of prokaryotic DNA was inserted into the baculovirus genome. The present viral homing vectors have an origin of replication and a selection marker encoded outside of the viral genome (FIG. 1). This design aspect of the present system is significant because of the different genome sizes of baculovirus and the viruses produced by the present invention. Baculovirus genome size is 130 kb, whereas, for example, adenovirus genome size is 36 kb. Furthermore, adenoviruses, retroviruses and AAV have tight upper size limits for packaging (see, e.g., (24)). Total capacity of retroviruses is generally limited to about 11 kb and of AAV is approximately 4.7 kb. Exemplified admids were capable of accepting up to about 6 kb of DNA into their attTn7 site. This limit can readily be increased by deleting additional Ad sequences, such as E4 or E2, which could be complemented by newer packaging cell lines (25, 26). Theoretical limits of about 36 kb are possible if new methods of packaging fully deleted Ads are perfected (27). The mini-Tn7 present in the admid transfer vectors (FIG. 2) was designed to be as small as possible. This was partially accomplished by removing the unnecessary dominant selectable marker from within the mini-Tn7.

Another significant design feature of the present inventive system is exemplified by the restriction enzyme site flanking the adenoviral genome in the admids. The restriction site allows the admid DNA to be linearized prior to transfection to maximize yield of recombinant virus. It was determined that the highest yields of recombinant virus were obtained when the recombinant admid was restricted at the 3' end of the recombinant Ad genome by PacI endonuclease. In those rare cases when the gene of interest has a recognition site for PacI the digestion can be omitted. If the linearization step is omitted then an additional round of amplification maybe preferable prior to large-scale virus production.

Figure 5A:
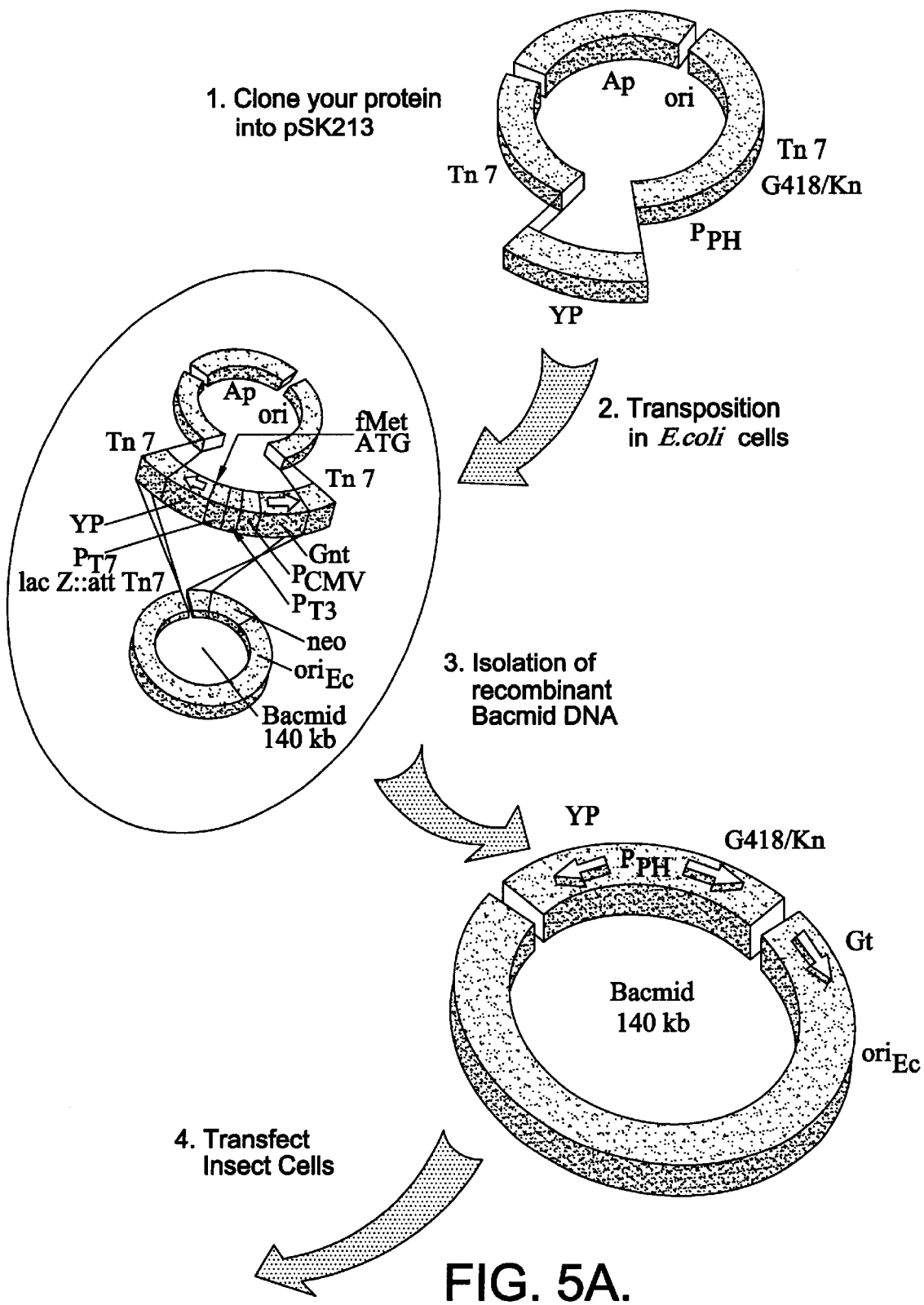
FIGS. 5A–5B. A. Flow Chart for Baculovirus Expression System. Donor plasmid pSK213 is transformed into strain, MW10Bacmid containing bMW2007 and pMON7124. Transposase encoded by pMON7124 supplies the enzymatic activity needed for transposition of the gene cassette contained within the Tn7L and Tn7R sequences on plasmid pSK213 to the homing site (lacZα region) encoded on the target baculovirus homing vector bMW2007. Interruption of the lacZα gene on the baculovirus homing vector is differentiated on plating medium containing the appropriate halogenated indigo dye dimer. DNA is isolated from the Lac⁻ host and used to transfect insect cells. B. Flow chart for use of the pSK213 system. Initial clones, after sequencing, can be used in expression studies in E. coli, baculovirus and tissue culture. Alternatively, the insert can be subcloned using SfiI/BamHI to a set of compatible plasmids.

Like the yeast (7) or *E. coli* homologous recombination systems (8–10), the present homing vector system yields clonal plasmids that avoid the need for time-consuming, costly, and labor-intensive rounds of plaque purification, and that are advantageous from a regulatory standpoint for gene therapy and vaccines. We estimate that the admid system of generating recombinant adenoviruses (FIG. 5) saves about 20 days over the 44-day conventional method of homologous recombination in 293 cells. This is because several time-consuming rounds of plaque purification in cell culture can be eliminated. As demonstrated in Table 3 below, the admid system saves 20 days and eliminates any risk of viruses being contaminated with replication competent adenovirus resulting from recombinogenic viral DNA.

TABLE 3

Time Line for Production of Recombinant Adenovirus*

| Admid method | Time | Time | Conventional method |
|---|---|---|---|
| Clone gene into transfer vector | 1 day | 1 day | Clone gene into transfer vector |
| transform DH10B Admid220 | 1 day | | |
| | | 2 days | Isolate plasmid, digest to linearize |
| Isolate DNA from white colonies, transform DH10B | 2 days | | |
| Isolate recombinant admid, digest with PacI | 2 days | | |
| Transfect 293 cells with recombinant admid, harvest virus | 6 days | 6 days | Transfect 293 cells with plasmid and recombinogenic viral DNA, harvest virus |
| | | 6 days | Plaque virus |
| | | 5 days | Amplify virus |
| | | 1 day | Prepare DNA, PCR to confirm insert |
| | | 6 days | Plaque virus |
| | | 5 days | Amplify virus |
| Prepare DNA, PCR to confirm insert | 1 day | 1 day | Prepare DNA, PCR to confirm insert |
| Amplify 2 times, titre amplified stock | 6 days | 6 days | Amplify 2 times, titre amplified stock |
| Large scale virus production, purification & titre | 5 days | 5 days | Large scale virus production, purification & titre |
| | 24 days | 44 days | |

*Admid system saves 20 days

Moving the promoter from the transfer vector onto the homing vector allows the production of an even more broadly useful, universal transfer vector for use in adenovirus, baculovirus, retrovirus, adeno-associated virus, *E. coli* and other expression systems (12). Such a "universal" vector can further speed up and lower the costs to express large amounts of functional protein for purification, or in vitro and in vivo functional analysis. Such increases in efficiency will be required to efficiently exploit the numerous new genes being discovered by the human genome project in a rapid, cost-effective drug development environment.

Example 4
System Using Universal Transfer Vector

The present invention provides the design, synthesis and use of a novel expression and cloning vector system that allows the identical protein to be expressed in *Escherichia coli*, mammalian, and insect cells. In the described vector, a series of species-specific promoters have been placed upstream of a shared ATG translational start site and SV40 poly(A) transcriptional termination signal. Specifically, the cytomegalovirus (CMV) immediate early-, baculovirus polyhedrin-, *E. coli* tac- and bacteriophage T7-promoters have been placed in series 5' to a shared ATG start codon. Induction of T7 RNA polymerase in appropriate host strains allows high-level bacterial expression of encoded protein. Composite baculovirus homing vector DNA produced by a Tn7-mediated transposition in *E. coli* and transfected into insect cells produce recombinant, infectious baculovirus which can be used to achieve high-level protein expression from the polyhedrin promoter. The CMV promoter, in this example, can be used to drive expression in transfected mammalian tissue culture cells, but does not transpose in this example. The CMV promoter can be used in the homing vector to promote expression from the virus. Additional features of this vector include color selection phenotype via interruption of an encoded B-galactosidase (BGal) gene when inserts are subcloned into the multiple cloning site, and the potential for protein fusion to a useful C-terminal peptide placed in an alternative (with respect to the BGal gene) reading frame. This C-terminal fusion includes a poly-histidine affinity tag for facile protein purification, cyclic AMP-dependent protein kinase phosphorylation sequence for in vitro protein labeling, and a thrombin cleavage site. A bifunctional (prokaryote and eukaryote) kanamycin/G418-resistance gene is encoded on the vector for use in the isolation of both transient and stable-transfected cell lines.

Traditional methods for expression of heterologous proteins involve subcloning the gene of interest into DNA vectors specific for the desired expression host. This requires either restriction digestion or PCR amplification of the gene, subcloning into an appropriate expression vector, and DNA sequence verification. All of these steps require an expenditure of both time and effort. To reduce the amount of subcloning needed we developed a single vector system capable of protein expression in three host systems commonly used for heterologous gene expression: *Escherichia coli*, baculovirus (Ayres), and mammalian tissue culture. The vector system was designed with the following criteria: i) a phenotypic color selection for positive cloning, ii) a multiple cloning site for both restriction enzyme and PCR cloning, iii) an affinity tag and C-terminal fusion, iv) antibiotic selection for both eukaryotic and prokaryotic organisms, v) proper splice sites and enhancers for mammalian tissue culture expression, and, vii) biosafety considerations to prevent recombinant virus-encoded protein expression in mammalian cells.

In order to effect efficient expression in all of the organisms used, we designed into the vector appropriate ribosomal entry sites, including a consensus Kozak sequence (Kozak, 1986) suitable for both insect and mammalian expression (see also Ayres), and ribosomal binding site optimized for *E. coli* (De Boer and Hui).

Since a major use of expression vectors is in obtaining sufficient protein for in vitro analysis, we decided to encode within the vector a useful affinity tag and the means for removing this tag from the purified protein. For maximum flexibility in protein expression, we chose to place the tag at the 3' end of the cloning site. The tag chosen was the polyhistidine tag (Hochuli) widely used in most laboratories today. The start site for protein translation (ATG) is at nucleotide 3947. Controlling elements include the CMV Intron/enhancer region (CMV IE), Tn7 right attachment site (Tn7R), polyhedron promoter ($P_{PH}$), lac promoter ($P_{lac}$), bacteriophage T7 promoter ($P_{T7}$), bacteriophage T3 promoter ($P_{T3}$) and CMV promoter ($P_{CMV}$), *E.coli* ribosome binding site (RBS), Thrombin cleavage site (TCS), multiple cloning site (MCS), polyhistidine coding sequence (His6) and the first and third translated reading frames corresponding to Bgal and the affinity tag fusion frames, respectively.

To achieve both BGal phenotypic selection and affinity tag fusion (without BGal fusion) the lacZα gene and the affinity tag were encoded in alternate translational reading frames (see FIG. 7). The vector (SEQ ID NO.:10) contains within the cloning site a means for translational reprogramming by altering the 3' reading frame of the protein (see Gesteland and Atkins). This reprogramming means allows one to design fusions that, depending on the fusion reading frame, can yield one of four possible 3' fusion peptides. A first fusion (corresponding to the first reading-frame) would keep the cloned protein in frame with the lacZ gene and generates a Bgal-fusion protein (SEQ ID NO.:11). A second fusion can be to encode a stop codon at the end of the cloned gene. We have termed this the zero reading frame fusion since it creates a precise termination.

Alternatives to the first and zero reading frames are second and third reading frame fusions at the 3' end of the cloned protein. At the 3' end of the SrfI PCR cloning site (located at the 5' end of the lacZa coding sequence, see FIGS. 4 and 7) we placed an affinity tag containing a fusion peptide (encoded entirely) within the third reading frame (+2 nucleotide bases) of the lacZα coding sequence. By placing this peptide out of frame (with respect to the lacZα gene), we permit both blue-white color selection and C-terminal peptide fusion.

The fusion peptide (SEQ ID NO.: 12) contains a thrombin cleavage site [Met-Tyr-Pro-Arg-Gly-Asn (SEQ ID NO.: 13), (where cleavage by thrombin occurs between the Arg and Gly residues)], multiple cloning site, cyclic AMP-dependent protein kinase (Kemptide; Leu-Arg-Arg-Ala-Ser-Leu-Gly (SEQ ID NO.: 14); Kemp, B. E. et al., Casnellie, J. E.) sequence, T3 RNA polymerase recognition site, and polyhistidine (His6, Hochuli et al., Smith et al.) affinity tag. The sequence of the third reading frame fusion is shown in FIG. 7 and provided as SEQ ID NO.: 12. In the lacZα reading frame this sequence encodes the protein of sequence: Met-Ala-Arg . . . Trp-Arg-Ser-Asn-Phe-Ter (see SEQ ID NO.:11; FIG. 7). Although it was designed to remain open, we have not incorporated any intentional designs into the second reading frame. In the anti-sense orientation, we have encoded a T3 promoter.

Example 4

Results pSK213 vector: general design features and construction. Using our above-mentioned design criteria, the baculoviral expression aspect of our vector system (pSK2 13, see FIG. 4) has several components needed to generate recombinant baculovirus in *E. coli* by a Tn7-mediated transposition event in a much shorter time period than required by standard homologous recombination transfection and plaque purification methods.

In the functional homing vector system, the transfer plasmid (having a Tn7 attachment site) is transformed into a strain of *E. coli* previously transformed for both a target plasmid ("homing vector") and a helper plasmid (encoding the genes needed for site-specific directional Tn7 transposition) (see Figure SA). In this *E. coli* host strain, transformed for all three plasmids, successful Tn7 transposition results in the disruption of the lacZ::attTn7 gene. The lacZ::attTn7 disruption can be differentiated on plates containing either BluoGal (LTI) or XGaI. Transfection of insect cells, such as either Spodoptera frugiperda or Trichoplusia ni, with composite baculovirus homing vector DNA generates recombinant, infectious baculovirus capable of producing high-level expression of encoded protein from the polyhedrin promoter.

Figure 4A:
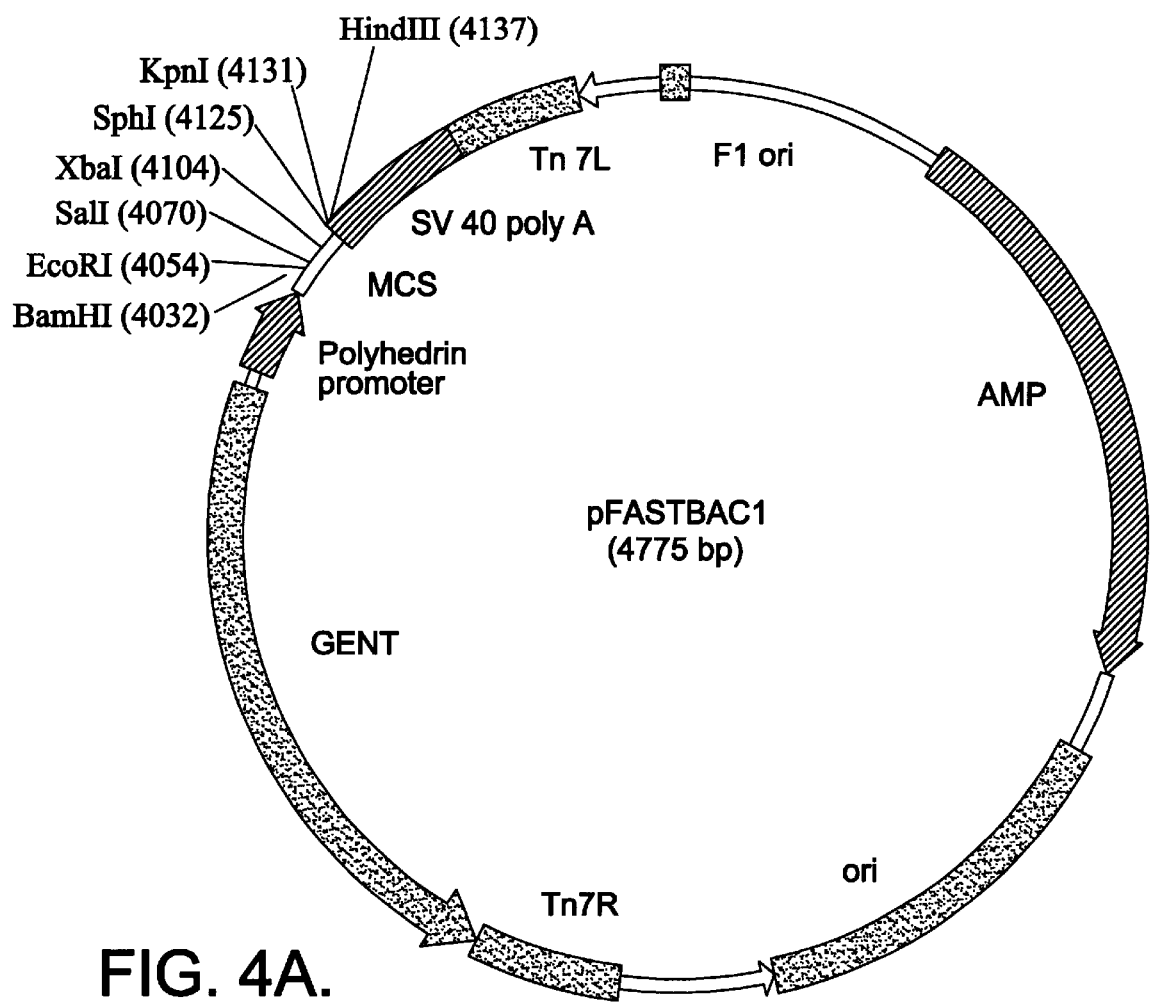
Figure 4B:
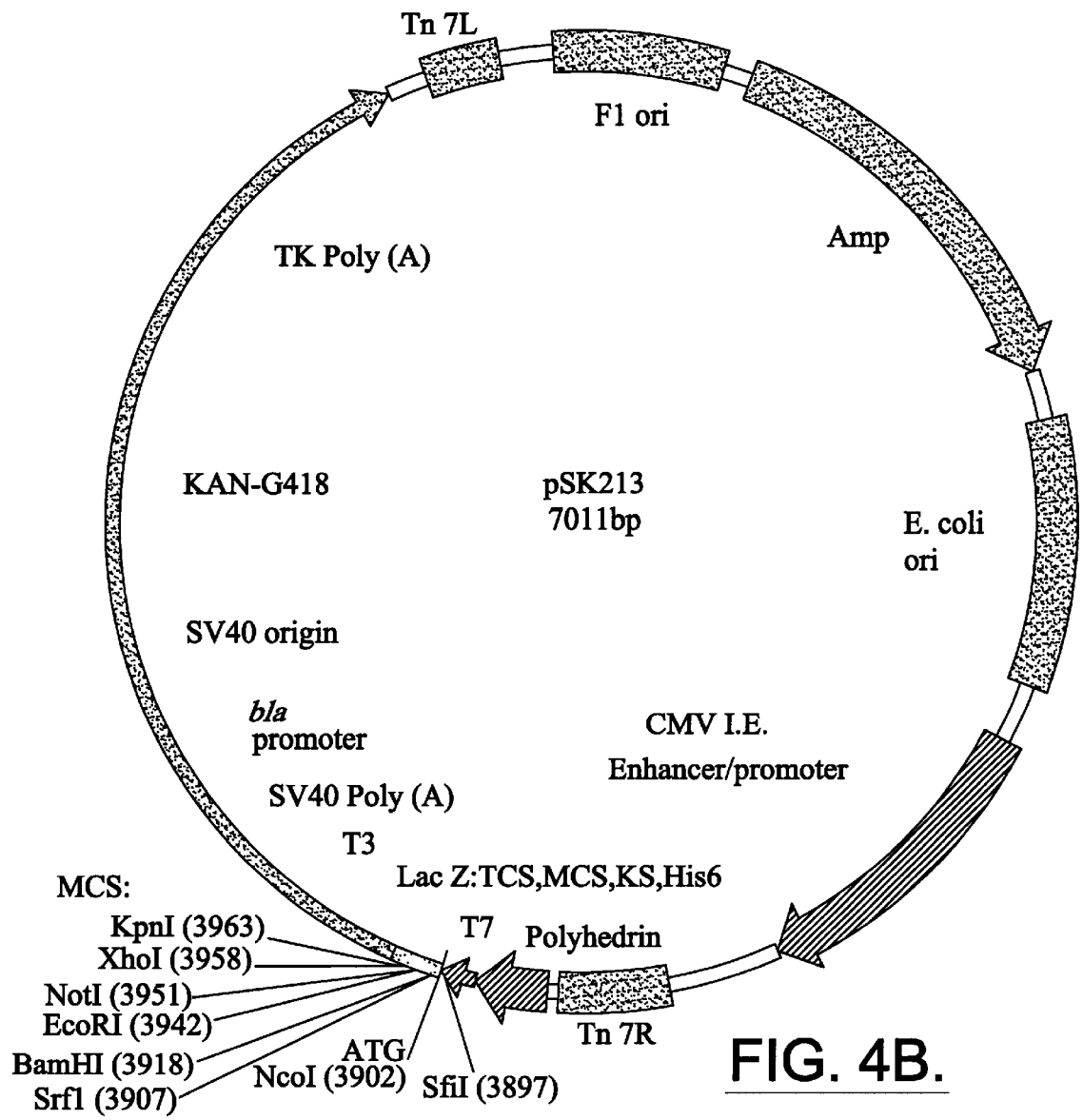

Because baculovirus is infectious for some mammalian cell lines (Boyce and Bucher, Hoffman et al.), we decided to place our mammalian expression components (specifically, the CMV promoter and 5' intron and enhancer regions) outside of the Tn7 transposition cassette (upstream of Tn7R, FIG. 4). This necessitates driving expression through the Tn7R region (discussed below). Additionally, it was found necessary to mutate several ATG codons to decrease translation initiating upstream from the desired fMet codon, which would inhibit production of the desired gene product.

Figure 5B:
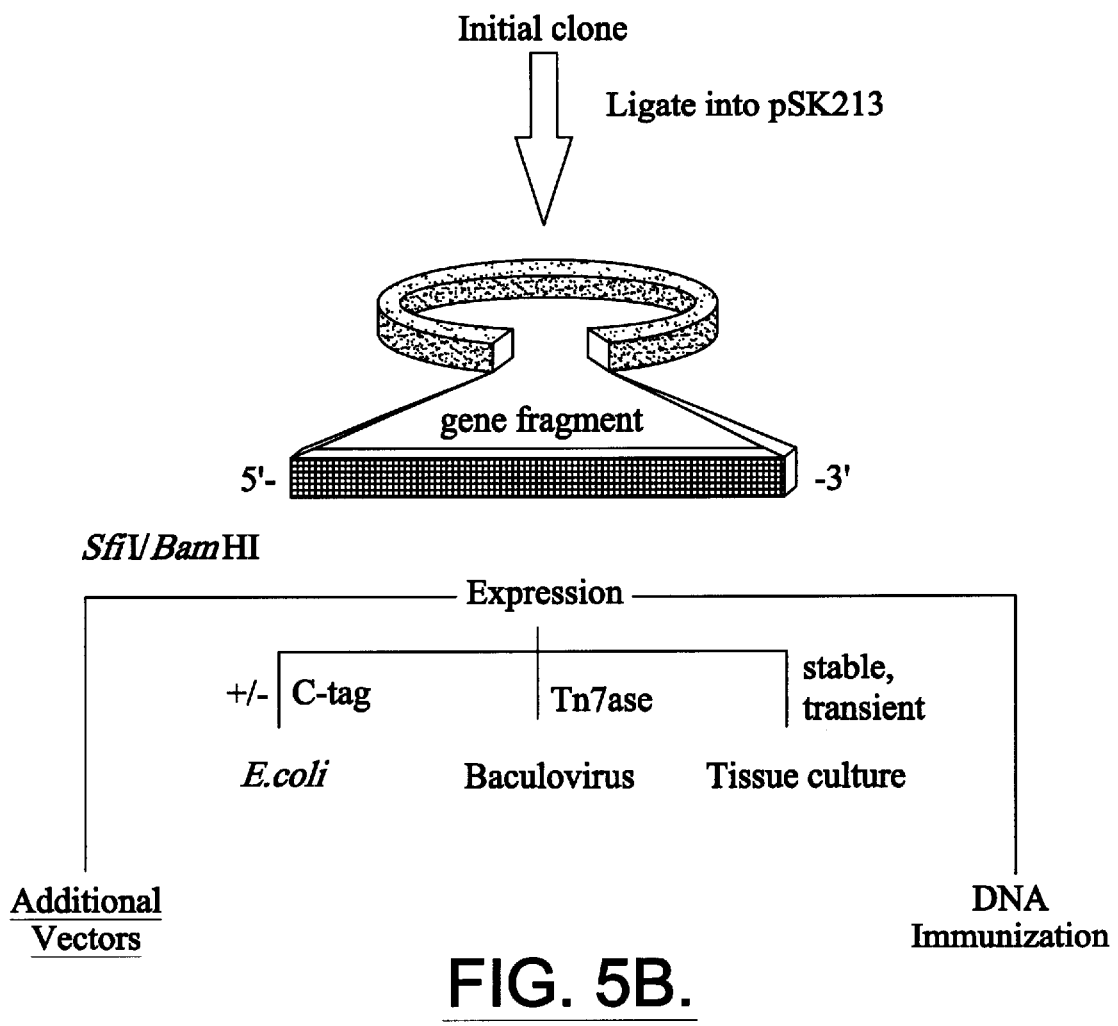

Shown in FIG. 5B is a flow chart of the potential uses for this vector in *E. coli*, insect and mammalian tissue culture cells.

Cloning and Blue/White Color Selection.

An initial version of the vector (pSK209) was constructed that contained a T7 promoter (Studier et al.) upstream of the lacZα gene. Initial cloning experiments showed that expression of lacZα was not high enough in this vector to allow detection of the Bgal phenotype on LB plating medium containing Xgal. We decided to place a synthetic tac promoter 5' to the T7 promoter to increase expression of Lac Z. The resultant vector containing tandem *E. coli* and T7 promoters has a blue/white color selection phenotype that is visually comparable to pCRScript (Weiner and Costa) on LB +Xgal plating medium.

At the ATG (fNet) start site we made allowance for both blunt-ended PCR cloning via a SrfI restriction enzyme site (5'-GCCCICCCG-3', Simcox et al.), and restriction enzyme cloning via SfiI (5'-GGCCNNNNNGGCC-3' (SEQ ID NO.:7)) and NcoI (5'-CCATGG-3') sites. The design of the fMet start site makes it possible to use the pSK213 vector for blunt-ended PCR cloning and initial gene expression with a 6 amino acid (aa) linker, and subsequent intramolecular ligation to generate a precise fusion. As described herein, the SfiI site has been designed to overlap with both the SrfI and NcoI sites (5'-GGCCACCATGGCCCGGGC-3' (SEQ ID NO.:8)). This allows PCR-derived clones containing a 5' sequence of 5'-NNGGCCACCATGGCC-3' (SEQ ID NO.:9) to be blunt-end cloned into the SrfI site. Expression in *E. coli*, insect and mammalian cells of this clone would result in a 6 aa N-terminal fusion [fMet and Ala from the initial ATG codon preceding the SrfI site, then either Leu, Pro, His, Gin or Arg (depending on the choice of NN at the 5' end of the PCR primer), followed by Gly, His, His, Gly, and then either Leu, Pro, His, Gln or Arg, (depending on the choice of NN); it is assumed that the fNet preceding the Ala will be removed by formyl-methionine peptidase]. Digestion with restriction enzyme SfiI at the two tandem sites and subsequent intramolecular ligation will result in both the loss of the 6 aa linker and a precise fusion. An analogous route can be performed with NcoI (although it would retain a 2–3 aa linker), but SfiI, an octomer-target recognizing restriction enzyme will likely be more useful. The pSK213 vector has been used for both blunt-ended SrfI PCR cloning and restriction enzyme cloning.

Both within and external to the lacZα gene we have incorporated restriction enzyme sites needed for compatibility with commercial cDNA library synthesis methods. These include methods for either partial or random fragments. Most of these will not have the translation-initiation sites needed for protein expression. Therefore, it is desirable to have an efficient translation start site available on the cloning vector. On pSK213 these sites (and commercial compatibility) include; XhoI/SalI [ZAP Express cDNA synthesis kits (Stratagene, La Jolla, Calif.)], EcoRI/XhoI [Uni- ZAP CDNA synthesis kits (Stratagene)], NotI/SalI [Superscript cDNA synthesis, (LTI, Gaithersburg, Md.)], and EcoRI/HindIll [for antisense directional cloning, (Novagen, Madison, Wis.)]. For full length cDNA cloning it is often desirable not to have an E. coli promoter, consensus Kozak sequence and ATG included 5' of the cDNA cloning site. Therefore, we have incorporated an Esp3AI site for full-length cDNA cloning. The restriction enzyme Esp3AI is an isocaudamer of EcoRI and so the pSK213 vector is compatible with EcoRI/XhoI-derived methods. This allows one to create one cDNA and clone it into the vector twice; once at the EcoRI site and including prokaryotic transcription, and a second time at the Esp3AI site and exclude transcription from occurring in E. coli.

Prokaryotic Expression.

The Cm$^r$ gene was cloned in-frame into both pSK213 and pRSET [from pBC SK+(Stratagene)] to synthesize the plasmids pSK215 and pRSETCat. These Cm$^r$-plasmids were transformed into the T7 RNA polymerase-encoding E. coli host strain BL21(DE3) (Studier et al.). The cells were grown to an $OD_{600}$ of 0.8, induced with IPTG (see Experimental protocol) and incubated with aeration for several hrs. Crude lysates and cleared supernatants of the induced cells were separated on a 4–20% Tris-glycine gel and the results (after Coomassie-blue staining of the gels) reviewed. The expression levels of Cm from the two plasmids are comparable.

Insect Expression and Design of the Baculovirus Homing Vector Host Strain.

One design criterion of the pSK213 system was to encode on the vector a bifunctional antibiotic resistance marker that would allow either transient or stable use of the vector in both E. coli and mammalian tissue culture. We chose to use the bifunctional pBK SK+-derived [Stratagene, Alting-Mees et al. (1992a and b)] aminoglycoside resistance marker [G418$^r$, Kn$^r$; driven by tandem B-lactamase and thymidine kinase r (tk) promoters]. This necessitated replacement of the Kn$^r$ gene on the 140 kb bMON14272 target baculovirus homing vector with a gentamicin (Gt$^r$) gene, and encoding on the pSK213 donor vector the Kn$^r$ gene (see Experimental protocol). Consideration was also given to prevent transcription-occlusion of expression from the SrfI site by placing all of the promoters (B-lactamase, tk, T7, tac, polyhedrin and CMV), in series. Site directed mutagenesis (SDM, Weiner et al.) was used to remove several ATG codons in the polyhedrin promoter.

Recombinant baculovirus homing vectors were generated from pSK215 and a control assembled to express the Cm gene product from the original, pFastBacl vector. This vector was renamed pFBCat. The experimental and control results are shown in FIG. 8B and demonstrate the ability of the pSK213 vector (pSK215, lanes 2 and 3) to give protein expression at a level comparable to pFastBac1 (pFBCat, lane 4).

Mammalian Expression.

The pSK213 vector and controls were transiently-transfected into a CV-1 cell line (see Experimental protocol) and examined for Cm gene expression by Western analysis using an antibody directed against the Cm protein. A control plasmid was synthesized to express the Cm gene expression from a pcDNA3 vector (Invitrogen, La Jolla, Calif.). This vector was renamed pcDNA3Cat.

A comparison of the expression levels of the Cm gene product for pSK213 and pcDNA3Cat revealed that although expression of the Cm gene product did occur, the expression levels were low compared to pcDNA3Cat. To determine if the decrease in expression was caused by the intervening sequence between the CMV promoter and translational start site, we created a series of 5' deletions and tested them for Cm gene product expression. These deletions demonstrated that within the 5' untranslated region of pSK213 there is a downward regulation of gene expression. Deletion of the entire 5' untranslated region brought expression levels back up to the amount found with pcDNA3Cat.

We performed site-directed mutagenesis to test whether the presence of multiple ATGs within the Tn7R region caused translation to initiate upstream from the desired start site, (Kozak, 1995). The results demonstrate that changing the 4 ATGs to GTG allowed efficient translation of the Cm gene product. Also, site-directed mutagenesis was used to change ATG DNA sequences to TTG between the CMV promoter and the first ATG of the Cm gene. The ATG of the BGal gene was changed to GTG, which is able to initiate protein translation in E.coli.

C-Terminal Fusion Peptide.

Figure 6:
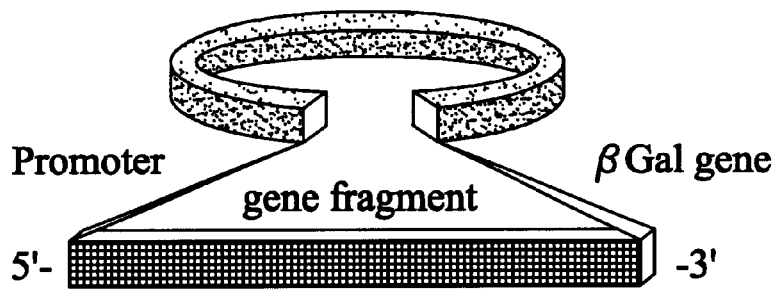
FIG. 6. Affinity tag purification and thrombin removal from E. coli supernatants in induced and uninduced cells. 3' bases at the fusion site determines the reading frame for cloned PCR products. Addition of two bases to the end of the cloned protein coding sequence adds 42 extra amino acids. This 3' addition encodes a thrombin cleavage site, Kemptide sequence and polyhistidine.

Fusion tags can play a critical role in protein purification. Encoding a tag at the C-terminus allowed us to produce a single vector that could be manipulated through subcloning to express a protein with or without fusion to a tag (see FIG. 6). To encode both a C-terminal affinity tag and BGal phenotypic color selection further necessitated that the tag be encoded in a lacZ-alternative (second) reading frame. This was accomplished by recoding (Gesteland and Atkins) the amino-terminus of the lacZα gene for functionality in two different (+1 and +2) reading frames. To accomplish that, we; i) designed the protein sequence, ii) encoded it using optimal E. coli codons (Sharp and Li), iii) removed all termination codons by replacing specific nucleotides in the wobble positions in the three reading frames, and iv) added two tandem termination codons (TAA) at the end of the C-terminal fusion that were themselves out-of-frame with respect to the lacZ gene itself. The affinity tag we chose was the polyhistidine (His6) sequence because of its small size, utility and widespread use (Hochuli et al.). We also chose a thrombin cleavage site for tag removal, and a Kemptide sequence (Leu-Arg-Arg-Ala-Ser-Leu-Gly (SEQ ID NO.:14), Kemp, B. E. et al., Casnellie, J. E.) for in vitro phosphorylation.

Example 4

Discussion

The present invention describes the design, generation and validation of a novel single vector system capable of expressing the same protein in mammalian tissue culture, insect cells and E. coli. We have placed a series of tandem promoters upstream of a shared start codon. Several of the tandem promoters have been placed within a transposition cassette able to directionally transpose to an attTn7 site located on a eukaryotic virus. By placing at least one of the promoters (PCMV(I/E)) external to the transposition cassette, we have shown that one can generate efficient protein synthesis through one half of the Tn region. Having shown this, other homing vectors containing different promoters located outside of the attTn7 site can readily be generated. In such a system, the steps can include cloning a gene into a transfer vector such as pSK213, and transforming that plasmid construct into one of several host strains. Each of the host strain separately can contain a different homing site-vector, each vector encoding a different promoter able to read through a successfully-transposed indicator gene:transposon attachment site (e.g., lacZα::attTn7 gene) In the present example, one further can remove the polyhedrin promoter from the pSK213 transfer vector and encode it on the baculovirus homing vector. Another baculovirus homing vector host strain will encode the basic promoter (Ayres). The present system advantageously allows one quickly to exchange promoters in the absence of any in vitro subcloning.

Additionally, different homing vectors themselves can be used to generate different viruses after eukaryotic transfection. These derivatives can include adenovirus, adeno-associated virus, retrovirus, baculovirus, Semliki Forest virus, and other vectors containing IRES sequences and other reporter groups.

Experimental Protocol

Enzymes.

SrfI and 10× Universal buffer were obtained from Stratagene (La Jolla, Calif.). Restriction enzymes were purchased from either New England Biolabs (Beverly, Mass.), Stratagene, Boehringer Mannheim, Gibco/BRL (Gaithersburg, Md.) or Promega (Madison, Wis.) and used according to manufacturers' directions. T4 DNA ligase (high concentration) and ligase buffer were purchased from Promega. PCR reactions containing a mixture of thermostable DNA polymerases Taq and Pfu (Barnes, Stratagene) were performed using buffers 3, 7 and 11 from the Optiprime kit (Stratagene).

Media.

Luria-Bertani (LB) medium contained tryptone (10 g $l^{-1}$), yeast extract (5 g $l^{-1}$), and NaCl (10 g $l^{-1}$). LB plates and 2xYT media were supplemented as indicated with ampicillin (Ap, Sigma) and methicillin (Mt, Sigma, 20 and 80 mg $1^{-1}$, respectively), for B-lactamase resistance, 25 mg $l^{-1}$ kanamycin (Kn, Sigma), 7 mg $l^{-1}$ gentamicin (Gt, Life Technologies), and 33 mg $l^{-1}$ chloramphenicol (Cm, Sigma).

Supplemented Grace's insect cell culture medium (Gibco/BRL) with 10% fetal bovine serum, 1× Pluronic F-68 (Gibco/BRL), and 10 μg ml $l^{-1}$ gentamicin (Gibco/BRL) was used for routine culturing of Sf9 cells. Dulbecco's Modified Eagle Medium (D-MEM) high glucose with 10% fetal bovine serum (Hyclone) was used for culturing CV-1 cells.

Plasmid Analysis.

The Wizard protocol (Promega) was used for mini-plasmid preparation according to the manufacturers direction. Plasmids were eluted from the olumns using room temperature (for plasmids under 10 kb) or 50° C. (for plasmids arger than 10 kb) in 10T1E (10 mM TrisHCl, pH 8.0, 1 mM EDTA). Qiagen-tip 500 (Qiagen, Chatsworth, Calif.) was used for large scale plasmid DNA purification.

Synthesis of pSK213. Plasmid vector pFastBac1 was obtained from Life Technologies, plasmids pBK-CMV and pBC SK(+) were obtained from Stratagene Cloning Systems, plasmid pCI-Neo and pCI-NeoCat were obtained from Promega Corp.

A series of synthetic oligonucleotides were cloned into pFastBacl 3' of the baculovirus polyhedrin promoter (Pbac), between the BamHI and HindIII sites. These oligonucleotides incorporated the following relevant regions downstream of the Pbac (from 5' to 3'): T7 promoter (PT7), the EcoRi isocaudamer Esp3I, E. coli Ribosome Binding Site (E.c.RBS), SfiI, Kozak site, ATG start site, NcoI, SrfI, BamHI, Thrombin Cleavage Site (TCS), Multiple Cloning Site (MCS), Kemptide, His6, HindIII. PCR was used to generate a fragment of the lacZα gene from plasmid pBK-CMV (Stratagene). The PCR primers used to generate the lacZα gene were designed to incorporate a 5' T3 promoter and 3' T7 transcription termination sequence. The generated fragment included the region from the T7 promoter through the SV40 poly(A) site. This PCR fragment was cloned into the HindIII site of the modified pFastBac1. Site directed mutagenesis (SDM, Weiner and Costa) was used to delete a 3' duplicated poly (A) site in the vector.

The sequence between the EcoRV site and the 5' side of the $P_{bac}$ (encoding the Gt$^r$ gene of pFastBac1) was replaced by a PCR-generated fragment encoding the Kn$^r$ gene of pBK-CMV. This Kn$^r$ cassette is able to express aminoglycosidase activity in both E. coli (Kn$^r$) and eukaryotes (G418$^r$).

A CMV immediate-early enhancer/promoter and a chimeric intron derived from the 5' donor site from the first intron of the human B-globin gene and the branch and 3'-acceptor site from the intron of an immunoglobulin gene heavy chain variable region were amplified from pCI-Neo and cloned into the pSK213-precursor vector upstream of the transposition cassette in an orientation such that it would support transcription in the direction of the lacZ gene. The four ATG sites within the Tn7R region were then each changed to TTG codons and the ability of this altered region tested for its ability to effect transposition in a bMW2010 host strain. Several derivatives of this construct were then tested for Cm gene expression in mammalian tissue culture.

Further SDM was used to remove 3 NcoI and 1 SfiI sites located in the plasmid outside of the multiple cloning site. The entire plasmid was completely sequenced to verify all intentional changes and to detect any unintentional changes.

Synthesis of GW10Baculovirus Homing Vector.

A PCR fragment encoding the Gtr gene was cloned from pFastBacl into a EcoRV-, Smal-digested pVL1393 (Luckow et al.). DH5α was chemically transformed with this ligation mixture. A transformed DH5a colony growing on LB plates containing both Gt and Ap was isolated and plasmid DNA purified from it and labeled pMW2000. Plasmid pFos1 (Kim et al., Shizuya et al.) was digested with SalI, the ends filled in with T4 DNA polymerase in the presence of dNTP, and cloned into pMW2000 that was both digested with EcoRi and blunt-ended with T4 DNA polymerase in the presence of dNTP. The resultant plasmid was labeled pMW2001. A lacZ::attTn7 fragment was generated by PCR of DH1OBaculovirus homing vector chromosomal DNA. This fragment was cloned into an EcoRi-digested, Pfu-DNA polymerase-treated (in the presence of dNTP) plasmid pMW2001. The resultant plasmid was labeled pMW2007. Plasmid pMW2007 was cotransfected with AcNPV DNA (Invitrogen) into Sf9 cells. Viral DNA from occlusion$^-$ viral transfectants was isolated and used to transform (by electroporation) E. coli strain DH10B (LTI) to both BGal$^+$ and Gt$^r$. This E. coli strain was labeled MW10Bacmid. Baculoviral DNA was isolated from MW10Bacmid and retransfected into Sf9 to verify the presence of infectious baculoviral DNA. Finally, E. coli strain MWlOBacmid was transformed to Tc$^r$ with pMON7124 helper plasmid DNA isolated from DH10Bacmid. The resultant strain was labeled GW10Bacmid and was used for subsequent baculoviral generation.

PCR Protocol and Pfu DNA Polymerase Polishing of Insert DNA.

PCR cycling was performed using a thermal oven (Idaho Technologies) in 10 l glass capillary tubes containing 10 μl reaction volume, or Stratagene Robocycler. The following parameters were generally used for PCR (Robocycler): 1 cycle of 94° C., 2 min.; 50° C. 2 min.; 70° C., 4 min., followed by 8–30 cycles of 94° C., 1 min.; 54° C., 2 min.; 70° C., 1 min. And in the thermal oven (Idaho Technologies): 1 cycle of 94° C., 15 sec.; 50° C., 0 sec.; 72° C., 1 min., followed by 8–30 cycles of 94° C., 2 sec.; 54° C., 2 sec.; 70° C., 90 sec. PCR reactions contained, per 10 μl volumes; 4 U of Taq DNA polymerase, 0.25 U of Pfu DNA polymerase, 250 μM dNTP (each), 0.1 μg each of primer, 1 μl of 10× buffer [either buffer 3, 7 or 11 from the Optiprime kit (Stratagene)], and 10–100 ng template.

PCR-mediated SDM was performed essentially as described (Weiner and Costa). The Cm gene from pBC-SK (+) was amplified by PCR using the oligonucleotides MW227 and MW228 (Costa and Weiner, 1994c). Where indicated, Pfu DNA polymerase was used to remove bases extended onto the end of PCR products prior to cloning (Costa and Weiner, 1994c).

Ligation Procedure and Transformation.

The standard pSK213 PCR ligation reactions were performed in 10 μl of 1× Universal buffer (Stratagene) containing 10 ng plasmid DNA, 50–200 ng Pfu end-polished PCR product, 500 nM ATP, 10 units SrfI and 4 units of T4 DNA ligase. The reaction was incubated for >1 hr at room temperature. Chemically-competent *E. coli* (40 μl, either DH10B or XL1Blue MRF') was transformed with 2 μl of a ligation reaction and plated onto LB plates spread with IPTG (30μ of 100 mM)+Xgal (30 μl of 10% stock solution in dimethylformamide, DMF) containing the appropriate antibiotic. The plates were incubated at 37° C. overnight and phenotypically BGal⁻ colonies were patched onto LB plates. Both colony PCR (Costa and Weiner, 1994b) and restriction digestion of mini-prep DNA was used for further analysis of cloned insert product.

Protein Induction in *E. coli* and Cat Activity Assay.

BL21 and BL21(DE3) competent cells (Novagen) were transformed with purified plasmid DNA and plated onto LB +Kn (30 μg ml⁻¹) plates overnight at 37° C. Single colonies were inoculated into 50 ml 2xYT +Kn, grown at 37° C. with aeration at 250 rpm to an $OD_{600}$ of 0.8. From this culture, 10 ml were placed into 2 x 50 ml flasks containing 2xYT. Next, 0.1 ml 100× IPTG stock solution (100 mM) was added to one flask (induced) and the other flask was left uninduced. Following growth at 37° C., 250 RPM for 3 hours, cells were pelleted and the media were discarded. Pellets were resuspended in 2.5 ml sonication buffer and sonicated by three 30 second pulses, placing samples back on ice for at least 1 min between pulses to prevent overheating. At the end of sonication, 200 μl crude lysate was frozen and the remaining sample was centrifuged at 11K rpm for 20 min.

Transposition and Isolation of Composite Baculovirus Homing Vectors.

Transposition, isolation of composite baculovirus homing vectors, composite baculovirus homing vector DNA purification, and transfection of Sf9 cells with baculovirus homing vector DNA was performed as described in the Bac-to-Bac baculovirus expression system manual (LTI).

Transfection and Expression in Insect Cells with Baculovirus Homing Vector DNA.

The transfection mixtures (2 ml) were harvested 48 hr post-transfection and used to infect 150 ml Sf9 cells at a density of $1\times10^6$ cells per ml. The media were collected and cleared of cells by centrifugation 5 days post-infection and titered. Time-course expression experiments were set up in T. ni insect cells at an multiplicity of infection (MOI) of 1, initial cell density of $1\times10^6$ cells per ml. For Western blots and stained gels, 1 ml samples were collected at 24 hr intervals for 4 days. Cells were gently pelleted, washed in cold PBS, and resuspended in 1 ml PBS. Proteins were solubilized in Laemmli loading buffer, boiled for 5 min, and separated by polyacrylamide gel electrophoresis on 4–16% Tris/Glycine polyacrylamide gels. The gels were either Coomassie stained or transferred by electroblotting onto nitrocellulose membranes. The membranes were blocked for 1 hr at 4° C. in Megga Block I (Cel Associates, Inc.), then incubated with unconjugated anti-CAT rabbit polyclonal primary antibody at a 1:5000 dilution in TBS-T (5 Prime, 3 Prime, Inc.). Anti-rabbit IgG alkaline phosphatase conjugate (Promega) was used as the secondary antibody. Proteins were detected with Western Blue (a stabilized substrate for alkaline phosphatase containing both nitro-blue tetrazolium salt and 5-bromo-4-chloro-3-indolyl-phosphate, Promega).

Transfection and Expression in Mammalian Tissue-Culture Cells.

African green monkey kidney (CV-1) cells were seeded at $1\times10^6$ cells per 100 mm tissue culture plate and transfected following the LipofectAMINE (Gibco/BRL) procedure for transient transfection of adherent cells. Specifically, 10 μg of plasmid DNA in 800 μl OptiMEM I Reduced Serum Medium (Gibco/BRL) and 104 μg of LipofectAMINE in 800 μl of OptiMEM were mixed and incubated at room temperature for 20 min, then diluted into 6.4 ml OptiMEM. Cells were washed 1× with OptiMEM, then overlaid onto the washed cells. The cells and transfection mixtures were incubated for 24 hr at 37° C. in a $CO_2$ incubator. After 24 hr, the transfection mixes were replaced with D-MEM supplemented with 10% fetal bovine serum, cells were placed back at 37° C. in a $CO_2$ incubator, and then harvested by scraping 48 hr. post-transfection, when cells were 80–90% confluent. Cell pellets were washed 1× in cold PBS. Cell lysates were prepared by resuspending cell pellets in 200 μl cold 1× PBS, then freezing on an ethanol-dry ice bath. The frozen pellets were then thawed at 37° C., and this freeze-thaw cycle was repeated 2 more times.

Throughout this application, various publication are referenced. These publications are each hereby incorporated by reference in their entirety.

While the invention has been described with respect to certain specific embodiments, it will be appreciated that many modifications and changes may be made by those skilled in the art without departing from the spirit of the invention. It is intended, therefore, by the appended claims, to cover all such modification and changes as fall within the true spirit and scope of the invention.

References

1. Kozarsky, K. F. and Wilson, J. M. (1993) Curr. Opinion Gen. Develop. 3, 499–503.
2. Zhao, H., Ivic, L., Otaki, J. M., Hashimoto, M., Mikoshiba, K., and Firestein S., (1998) Science 279, 237–242.
3. Noel, R. J., Antinozzi, P. A., McGarry, and Newgard, C. B. (1997) J. Biol. Chem. 272, 18621–18627.
4. Imler, J. -L. (1995) Vaccine 13, 1143–1151.
5. Lamarche, N., Massie, B., Richer, M., Paradis, H., and Langelier, Y. (1990) J. Gen. Virol. 71, 1785–1792.
6. Berkner, K. L. (1988) BioTechniques 6, 616–229.
7. Ketner, G., Spencer, F., Tugendreich, S., Connelly, C., and Hieter, P. (1994) Proc. Natl. Acad. Sci. USA 91, 6186–6190.
8. Chartier, C., Degryse, E., Dieterle, A., Pavirani, A. and Mehtali, M. (1996) J. Virol 70, 4805–4810.
9. Crouzet, J., Naudin, L., Orsini, C., Vigne, E., Ferrero, L., Le Roux, A., Benoit, P., Latta, M., Torrent, C., Branellec, D., Denefle, P., Mayaux, J. -F., Perricaudet, M, and Yeh, P. (1997) Proc. Natl. Acad. Sci. USA 94, 1414–1419.
10. He, T. -C., Zhou, S., da Costa, L. T., Yu., J., Kinzler, K. W., and Vogelstein, B. (1998) Proc. Natl. Acad. Sci. USA 95, 2509–2514.
11. Luckow, V. A., Lee, S.C., Barry, G. F., and Olins, P. O. (1993) J. Virol. 67, 4566–4579.
12. Weiner, M. (manuscript in preparation).
13. Barry, G. F. (1988) Gene 71: 75–84.
14. Hanahan, D. (1983) J. Mol. Biol. 166, 557–580.
15. Gossen, M. and Bujard, H. (1992) Proc. Natl. Acad. Sci. USA 89, 5547–5551.

16. Kim, U. -J., Shizuya, H., deJong, P. J., Birren, B., and Simon, M. L. (1992) Nuc. Acids Res. 20, 1083–1085.
17. Hearing, P. and Shenk, T. (1983) Cell 33, 695–703.
18. Graham, F. L., Smiley, J., Russell, W. C., and Naim, R. (1977) J. Gen. Virol. 36, 59–72.
19. Nichols, W. W., Murphy, D. G., Cristofalo, V. J., Toji, L. H., Greene, A. E., and Dwight, S. A. (1977) Science 196, 60–63.
20. Current Protocols in Molecular Biology (1995) ed. Ausubel, F. M., Brent, R., Kingston, R. E., Moore, D. D., Seidman, J. G., Smith, J. A., and Struhl, K. John Wiley & Sons.
21. Bett, A. J., Krougliak, V., and Graham, F. G. (1995) Virus Res. 39, 75–82.
22. Ghersa, P., Hooft van Huijsduijnen, R., Whelan, J., Cambet, Y., Pescini, R., and DeLamarter, J. F. (1994) J. Biol. Chem. 269, 29129–29137.
23. Ad purification
24. Bett, A. J., Prevec, L., and Graham, F. L. (1993) J. Virol. 67, 5911–5921.
25. Brough, D. E., Lizonova, A., Hsu, C., Kulesa, V. A., and Kovesdi, I. (1996) J. Virol. 70, 6497–6501.
26. Amalfitano, A., Hauser, M. A., Hu, H., Serra, D., Begry, C. R., and Chamberlain, J. S. (1998) J. Virol. 72, 26–933.
27. Kochanek, S., Clemens, P. R., Mitani, K., Chen, H. -H., Chan, S., and Caskey, C. T. (1996) Proc. Natl. Acad. Sci. 93, 5731–5736
28. Alting-Mees, M. A., P. Hoener, D. Ardoural, J. Sorge, and J. M. Short. (1992a) Zap Express and pBK-CMV, pBK-RSV phagemid vectors for prokaryotic and eukaryotic expression. Strategies in Molecular Sciences. 5:58–61.
29. Alting-Mees, M. A., J. A. Sorge, and J. M. Short. (1992b) pBlueScript II: Multifunctional cloning and gene mapping vectors. Methods in Enzymology. 216:488–495.
30. Ayres, M. D., S. C. Howard, J. Kuzio, M. Lopez-Ferber and R. D. Possee. (1994) The complete DNA sequence of Autographa californica nuclear polyhedrosis virus. Virology. 202:586–605.
31. Barnes, W. M. (1994) PCR amplification of up to 35-kb DNA with high fidelity and high yield from ☐ bacteriophage templates. Proc. Natl. Acad. Sci. USA. 91:2216–2220.
32. Boyce, F. And N. L. Bucher. (1996) Baculovirus-mediated gene transfer into mammalian cells. Proc. Natl. Acad. Sci. U.S.A. 93:2348–2352.
33. Casnellie, J. E. (1991) Assay of protein kinases using peptides with basic residues for phosphocellulose binding. Methods in Enzymology 200:115.
34. Costa, G. L. and M. P. Weiner. (1994a) Rapid screening for inserts and insert orientation in plasmid DNA by colony PCR. Strategies in Mol. Biol. 7:35–37.
35. Costa, G. L. and M. P. Weiner. (1994b) Protocols for cloning and analysis of PCR-generated DNA fragments. PCR Methods and Applications, Cold Spring Harbor Press. 3:S95-S106.
36. Costa, G. L. and M. P. Weiner. (1994c) Polishing of PCR fragments with either T4 or Pfu polymerase improves the efficiency of blunt-ended cloning. Nucleic Acids Research. 22:2423.
37. Craig, N. L. (1989) Transposon Tn7. In: Berg, D. E. and M. M. Howe (eds), Mobile DNA. American Society for Microbiology, Washington, D.C. pp.211–225.
38. De Boer, H. A. and A. S. Hui. (1990) Sequences within ribosome binding site affecting messenger RNA translatability and method to direct ribosomes to single messenger RNA species. Methods in Enzymology. 185:103–114.
39. Gesteland, R. F. and J. F. Atkins (1996) RECODING: Dynamic reprogramming of translation. Annu.Rev.Biochem. 65:741–768.
40. Hochuli, E., W. Bannwarth, H. Dobeli, R. Gentz and D. Stuber (1988) Genetic approaches to facilitate purification of recombinant proteins with a novel metal chelate adsorbant. Bio/Technology. 6:1321–1325.
41. Hoffman, C., V. Sandig, G. Jennings, M. Rudolph, P. Schlag and M. Strauss. (1995). Efficient gene transfer into human hepatocytes by baculovirus vectors. Proc. Natl. Acad. Sci. U.S.A. 92:10099–10103.
42. Kemp, B. E., D. J. Graves, E. Benjamini and E. G. Krebs. (1977) Role of multiple basic residues in determining the substrate specificity of cyclic AMP-dependent protein kinase. J.Biol.Chem. 252:4888.
43. Kim, U. -J., H. Shizuya, P. de Jong, B. Birren, and M. I. Simon (1992) Stable propagation of cosmid-sized human DNA inserts in an F-factor based vector. Nucleic Acids Research. 20:1083–1085.
44. Kozak, M. (1986) An analysis of 5' noncoding sequences from 699 vertebrate messenger RNAs. Nucleic Acids Research 15:8125–8148.
45. Kozak, M. (1995) Adherence to the first-AUG rule when a second AUG codon follows closely upon the first. Proc. Natl. Acad. Sci. U.S.A. 92:2662–2666.
46. Leusch, M. S., S. C. Lee and P. O. Olins. (1995) A novel host-vector system for direct selection of recombinant baculoviuses (bacmids) in Escherichia coli. Gene. 160:191–194.
47. Ooi, B. G., C. Rankin and L. K. Miller. (1989) Downstream sequences augment transcription from the essential initiation site of a baculovirus polyhedrin gene. J. Mol. Biol. 210:721–736.
48. Possee, R. D. and S. C. Howard. (1987) Analysis of the polyhedrin gene promoter of the Autographa californica nuclear polyhedrosis virus. Nucleic Acids Research. 15:10233–10248.
49. Rankin, C., B. G. Ooi and L. K. Miller. (1988) Eight base pairs encompassing the transcriptional start point are the major determinant for the baculovirus polyhedrin gene expression. Gene 70:39–49.
50. Sharp, P. M. and H. -W. Li. (1986) Codon usage in Escherichia coli does not reflect selection for 'rare' codons. Nucleic Acids Research 14:7737–7749.
51. Shizuya, H., B. Birren, U. -J. Kim, V. Mancino, T. Slepak, Y. Tachiiri, and M. I. Simon (1992) A bacterial cloning system for cloning large human DNA fragments. Proc. Natl. Acad. Sci., USA. 89:8794–8797.
52. Simcox, T., S. Marsh, E. Gross, W. Lernhardt, S. Davis and M. Simcox. (1991) SrfI, a new type-II restriction endonuclease that recognizes the octanucleotide sequence, 5'-GCCCIGGGC-3'. Gene 109:121–123.
53. Smith, M. C., T. C. Furman, T. D. Ingolia, and C. Pidgeon (1988) Chelating peptide-immobilized metal ion affinity chromatography. J.Biol.Chem. 263:7211–7215.
54. Studier, F. W., A. H. Rosenberg, J. J. Dunn and J. W. Dubendorff (1990) Use of T7 RNA polymerase to direct expression of cloned genes. Methods in Enzymology. 185:60–89.
55. Weiner M. P., G. L. Costa, W. Schoettlin, J. Cline, E. Mathur, and J. Bauer (1994). Site-directed mutagenesis of plasmid DNA using the polymerase chain reaction. Gene. 151:119–123.

What is claimed is:

1. An isolated nucleic acid for generating a recombinant animal virus comprising
   a) an animal virus polynucleotide wherein the viral polynucleotide comprises viral elements sufficient for recombinant viral production in a host cell upon contact with replication proteins of the virus;
   b) a transposon target site within the viral polynucleotide wherein location of the transposon target site within the viral polynucleotide does not prevent recombinant virus production in a host cell upon contact with viral replication proteins; and
   c) an origin of replication.

2. The nucleic acid of claim 1, wherein the virus is selected from the group consisting of adenovirus, retrovirus and adeno-associated virus.

3. The nucleic acid of claim 1, wherein the virus is adenovirus.

4. The nucleic acid of claim 1, wherein the origin of replication is inserted in a region outside of the viral polynucleotide.

5. The nucleic acid of claim 1, wherein the origin of replication is derived from a bacterial origin selected from the group consisting of F, colE1, pl5A and fl.

6. The nucleic acid of claim 1, wherein the origin of replication is derived from a yeast origin selected from the group consisting of cen3, cen4, cen and two micron.

7. The nucleic acid of claim 1, further comprising a selection marker.

8. The nucleic acid of claim 1, further comprising a functional promoter, wherein upon transposition of an exogenous nucleic acid into the transposon target site, the promoter is positioned to promote expression of the exogenous nucleic acid.

9. The nucleic acid of claim 1, wherein the transposon target site is a Tn7 attachment site.

10. The nucleic acid of claim 1, further comprising an indicator gene within the viral polynucleotide wherein the transposon target site is inserted within the indicator gene, wherein transposition of an exogenous nucleic acid into the transposon target site disrupts expression of the indicator gene, and wherein location of the indicator gene within the viral polynucleotide does not prevent recombinant virus production in a host cell upon contact with viral replication proteins.

11. The nucleic acid of claim 1, wherein a functional ATG codon within the transposon target site has been rendered non-functional.

12. The nucleic acid of claim 1, further comprising a transposon inserted into the transposon target site, wherein the transposon comprises an exogenous nucleic acid.

13. A cell comprising the nucleic acid of claim 1.

14. A method of producing a recombinant animal virus comprising (a) contacting the nucleic acid of claim 1, in a cell under conditions suitable for transposition, with a transfer vector, wherein the transfer vector comprises
   (i) a transposon that recognizes the transposon target site,
   (ii) an exogenous polynucleotide inserted between a left and of the transposon and a right end of the transposon,
   (iii) a bacterial origin of replication positioned outside of a region encompassed by the left end and the right end of the transposon, and
   (iv) a selectable marker, to produce a transposition product; and
(b) transferring the transposition product into a cell comprising any necessary viral replication proteins, thereby producing the virus.

15. The nucleic acid of claim 3, wherein the adenovirus is selected from the group consisting of Ad2 and Ad5.

16. The nucleic acid of claim 3, wherein the adenovirus is Ad5.

17. The nucleic acid of claim 3, wherein the E1 region of adenovirus is deleted from the adenoviral polynucleotide.

18. The nucleic acid of claim 3, wherein the E3 region of adenovirus is deleted from the adenoviral polynucleotide.

19. The nucleic acid of claim 3, wherein the E1 region and the E3 region of adenovirus is deleted from the adenoviral.

20. The nucleic acid of claim 7, wherein the selection marker is inserted in a region outside of the viral polynucleotide.

21. The nucleic acid of claim 8, wherein the promoter is a eukaryotic promoter.

22. The nucleic acid of claim 8, wherein the promoter is a prokaryotic promoter.

23. The nucleic acid of claim 10, wherein the indicator gene is a lac Z gene. polynucleotide.

24. The nucleic acid of claim 10, wherein the virus is adenovirus and wherein the indicator gene replaces the E1 region of the adenoviral polynucleotide.

25. The nucleic acid of claim 10, wherein the exogenous nucleic acid encodes a polypeptide.

26. The nucleic acid of claim 10, wherein the exogenous nucleic acid encodes an antisense nucleic acid.

27. The nucleic acid of claim 10, wherein the exogenous nucleic acid encodes an aptamer.

28. The nucleic acid of claim 10, wherein the exogenous nucleic acid lacks a promoter.

29. The method of claim 14, wherein the nucleic acid further comprises a promoter inserted in a region within the viral polynucleotide and positioned to promote expression of the exogenous polynucleotide.

30. The method of claim 14, wherein the nucleic acid further comprises a promoter inserted in a region outside of the viral polynucleotide and positioned to promote expression of the exogenous polynucleotide.

31. The method of claim 14, wherein the exogenous polynucleotide lacks a promoter.

32. The method of claim 14, wherein a functional ATG codon within the transposon has been rendered non-functional.

33. The method of claim 14, wherein the transfer vector further comprises a promoter outside the region encompassed by the left end and the right end of the transposon, positioned to promote expression of an exogenous polynucleotide inserted in the cloning site.

34. The method of claim 14, wherein the transfer vector further comprises two or more promoters derived from two or more organisms, wherein the promoters are outside the region encompassed by the left end and the right end of the transposon and are positioned to promote expression of an exogenous polynucleotide inserted in the cloning site.

35. The method of claim 14, wherein the transfer vector further comprises a promoter within the region encompassed by the left end and the right end of the transposon, positioned to promote expression of an exogenous polynucleotide inserted in the cloning site.

36. The method of claim 35, wherein the promoter is a cytomegalovirus promoter.

37. A kit for producing a recombinant animal virus comprising
   a) a nucleic acid for generating a recombinant animal virus comprising
      (i) an animal virus polynucleotide wherein the viral polynucleotide comprises viral elements sufficient for recombinant viral production in a host cell upon contact with replication proteins of the virus;
      (ii) a transposon target site within the viral polynucleotide wherein location of the transposon target site within the viral polynucleotide does not prevent recombinant virus production in a host cell upon contact with viral replication proteins; and
      (iii) an origin of replication; and
   b) a vector for transposition of an exogenous nucleic acid, comprising
      (i) a transposon that recognizes the transposon target site, wherein the transposon has a cloning site between a left end of the transposon and a right end of the transposon;
      (ii) a bacterial origin of replication positioned outside of a region encompassed by the left end and the right end of the transposon; and
      (iii) a selectable marker.

38. The kit of claim 37, further comprising a host cell comprising a nucleic acid encoding a transposase functional for transposition of the transposon.

39. A vector for transposition of an exogenous nucleic acid, comprising
   (a) a transposon having a cloning site between a left end of the transposon and a right end of the transposon;
   (b) a bacterial origin of replication positioned outside of a region encompassed by the left end and the right end of the transposon;
   (c) a promoter outside the region encompassed by the left end and the right end of the transposon, positioned to promote expression of an exogenous polynucleotide inserted in the cloning site; and
   (d) a selectable marker.

40. The vector of claim 39, wherein a functional ATG codon within the transposon has been rendered non-functional.

41. The vector of claim 39, wherein the selectable marker is inserted outside of the region encompassed by the left and right end of the transposon.

42. The vector of claim 39, further comprising an exogenous polynucleotide inserted in the cloning site, wherein the exogenous polynucleotide encodes a polypeptide.

43. The vector of claim 39, further comprising an exogenous polynucleotide inserted in the cloning site, wherein the exogenous polynucleotide encodes an antisense nucleic acid.

44. The vector of claim 39, further comprising an exogenous polynucleotide inserted in the cloning site, wherein the exogenous polynucleotide encodes an aptamer.

45. The vector of claim 39, wherein the transposon is Tn7.

46. A cell comprising the vector of claim 39.

47. A vector for transposition of an exogenous nucleic acid, comprising
   (a) a transposon having a cloning site between a left end of the transposon and a right end of the transposon;
   (b) a bacterial origin of replication positioned outside of a region encompassed by the left end and the right end of the transposon;
   (c) two or more promoters derived from two or more organisms, wherein the promoters are outside the region encompassed by the left end and the right end of the transposon and are positioned to promote expression of an exogenous polynucleotide inserted in the cloning site; and
   (d) a selectable marker.

48. A vector for transposition of an exogenous nucleic acid, comprising
   (a) a transposon having a cloning site between a left end of the transposon and a right end of the transposon;
   (b) a bacterial origin of replication positioned outside of a region encompassed by the left end and the right end of the transposon;
   (c) an exogenous polynucleotide inserted in the cloning site, wherein the exogenous polynucleotide lacks a promoter; and
   (d) a selectable marker.

49. The vector of claim 48, further comprising a cytomegalovirus promoter inserted between the left and right end of the transposon, positioned to promote expression of the exogenous polynucleotide.

* * * * *

UNITED STATES PATENT AND TRADEMARK OFFICE
CERTIFICATE OF CORRECTION

PATENT NO.    : 6,291,214 B1
DATED         : September 18, 2001
INVENTOR(S)   : Richards et al.

It is certified that error appears in the above-identified patent and that said Letters Patent is hereby corrected as shown below:

<u>Column 13,</u>
Lines 38-39, "5'-CGGTCGACCG (New England Biolabs)" should read
-- (New England Biolabs) --

<u>Column 45,</u>
Line 7, " left and" should read -- left end --
Line 26, "adenoviral." should read -- adenoviral polynucleotide. --
Line 35, "gene. polynucleotide." should read -- gene. --

Signed and Sealed this

Eleventh Day of February, 2003

JAMES E. ROGAN
*Director of the United States Patent and Trademark Office*